United States Patent
Heuer et al.

(10) Patent No.: US 6,534,200 B1
(45) Date of Patent: Mar. 18, 2003

(54) ELECTROLUMINESCENT SYSTEMS WITH POLYNULCEAR METAL COMPLEXES

(75) Inventors: Helmut-Werner Heuer, Krefeld (DE); Rolf Wehrmann, Krefeld (DE); Andreas Elschner, Mülheim (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/763,893

(22) PCT Filed: Aug. 20, 1999

(86) PCT No.: PCT/EP99/06125

§ 371 (c)(1), (2), (4) Date: Feb. 28, 2001

(87) PCT Pub. No.: WO00/14173

PCT Pub. Date: Mar. 16, 2000

(30) Foreign Application Priority Data

Sep. 2, 1998 (DE) ......................................... 198 39 946

(51) Int. Cl.$^7$ ............................................. H05B 33/00
(52) U.S. Cl. ....................... 428/690; 313/504; 313/506; 428/704; 428/917
(58) Field of Search ................................ 428/690, 917, 428/704; 313/504, 506

(56) References Cited

U.S. PATENT DOCUMENTS

| | | | |
|---|---|---|---|
| 4,539,507 A | 9/1985 | Van Slyke et al. | 313/504 |
| 4,720,432 A | 1/1988 | Van Slyke et al. | 428/457 |
| 4,769,292 A | 9/1988 | Tang et al. | 428/690 |
| 4,885,211 A | 12/1989 | Tang et al. | 428/457 |
| 4,923,288 A | 5/1990 | Allen et al. | 350/355 |
| 4,923,774 A | 5/1990 | Van der Auweraer et al. | 430/59 |
| 4,959,430 A | 9/1990 | Jonas et al. | 526/257 |
| 4,987,042 A | 1/1991 | Jonas et al. | 429/213 |
| 5,035,926 A | 7/1991 | Jonas et al. | 427/393.1 |
| 5,059,863 A | 10/1991 | Tashiro et al. | 313/504 |
| 5,077,142 A | 12/1991 | Sakon et al. | 428/690 |
| 5,154,796 A | 10/1992 | Kuniya et al. | 156/603 |
| 5,164,005 A | 11/1992 | Kuske et al. | 106/459 |
| 5,247,190 A | 9/1993 | Friend et al. | 257/40 |
| 5,281,489 A | 1/1994 | Mori et al. | 428/690 |
| 5,300,575 A | 4/1994 | Jonas et al. | 525/186 |
| 5,317,169 A | 5/1994 | Nakano et al. | 257/40 |
| 5,328,809 A | 7/1994 | Holmes et al. | 430/321 |
| 5,399,502 A | 3/1995 | Friend et al. | 437/1 |
| 5,401,827 A | 3/1995 | Holmes et al. | 528/374 |
| 5,408,109 A | 4/1995 | Heeger et al. | 528/40 |
| 5,425,125 A | 6/1995 | Holmes et al. | 385/143 |
| 5,466,392 A | * 11/1995 | Hironaka et al. | 252/301.16 |
| 5,484,922 A | 1/1996 | Moore et al. | 46/7 |
| 5,487,953 A | * 1/1996 | Shirota et al. | 428/690 |
| 5,512,654 A | 4/1996 | Homes et al. | 528/373 |
| 5,672,678 A | 9/1997 | Holmes et al. | 528/373 |
| 5,726,457 A | 3/1998 | Nakano et al. | 257/40 |
| 5,766,515 A | 6/1998 | Jonas et al. | 525/500 |
| 5,869,350 A | 2/1999 | Heeger et al. | 438/29 |
| 6,083,635 A | 7/2000 | Jonas et al. | 428/690 |
| 6,169,163 B1 | * 1/2001 | Woo et al. | 528/397 |

FOREIGN PATENT DOCUMENTS

| | | |
|---|---|---|
| DE | 42 11 459 | 10/1993 |
| EP | 579151 | 1/1994 |
| EP | 765106 | 3/1997 |
| EP | 817540 | 1/1998 |
| WO | 98/36035 | 1/1998 |

OTHER PUBLICATIONS

Advanced Materials (month unavailable) 1992, pp. 36–37, G. Grem, et al, Realization of a Blue–Light–Emitting Device Using Poly (p–phenylene).

J. Chem. Soc., Chem. Commun. 32, (month unavalable), pp. 32–34,P. L. Burn, et al, "Synthesis of a Segmented Conjugated Polmer Chain Giving a Blue Shifted Electroluminescence and Improved Efficiency".

Polymer, Jun., 1990, pp. 1137–1141, S. Tokito et al, "Polyarylenevinylene films prepared from precursor polymers soluble in organic solvents".

Physical Review B, vol. 42, No. 18, Dec. 15, 1990, pp. 11 670–11 681, N. F. Colaneri et al, "Photoexicited states in poly (p–phenylene vinylene): Comparison with trans, trans–distyrylbenzene, a model ologomer".

Pure & Applied Chem., vol. 67, No. 1 (month unavailable), 1995, pp. 175–182, G. E. Johnson, et al, "Electroluminescence from single layer molecularly doped polymer films".

Adv. Materials, 7, No. 6, (month unavailable) 1995, pp. 551–554,J. Pommerehne et al, "Efficient Two Layer LEDs on a Polymer Blend Basis".

Appl. Phys. Lett., 67(16), (month unavailable) 1995, pp. 2281–2283, J. Kido et al, "Single–layer white light–emitting organic electroluminescent devices based on dye–dispersed poly(N–vinylcarbazole)".

J. Phys. Chem. (month unavailable) 1993, pp. 6240–6248, K. Naito et al, "Molecular Design for Nonpolymeric Organic Dye Glasses with Thermal Stability: Relations between Thermodynamic Parameters and Amorphous Properties".

(List continued on next page.)

*Primary Examiner*—Cynthia H. Kelly
*Assistant Examiner*—Dawn Garrett
(74) *Attorney, Agent, or Firm*—Godfried R. Akorli; Diderico van Eyl; John E. Mrozinski, Jr.

(57) ABSTRACT

Electroluminescent assembly comprising a substrate, an anode, an electroluminescent element and a cathode, where at least one of the two electrodes is transparent in the visible spectral region and the electroluminescent element comprises one or more zones selected from the group consisting of a hole injection zone, a hole transport zone, an electroluminescent zone, an electron transport zone and an electron injection zone in the specified order, where each of the zones present may also assume functions of the other zones mentioned, wherein the electroluminescent element contains a multinuclear metal complex.

22 Claims, No Drawings

OTHER PUBLICATIONS

Hauben–Weyl, 4/1C, Ullmann (4)13, date unavailable) Dr. F. J. Bröcker, "Hydrierung und Dehydrierung, katalytische".

Appl. Phys. Lett. 66(20), May 15, 1995, pp. 2679–2681, C. Adachi et al, "Molecular design of hole transport materials for obtaining high durability in organic electroluminescent diodes".

Hauben–Weyl. Methoden der organischen Chemie, vol. E20, Makromolekulare Stoffe, Past 2 (month unavailable) 1987, pp. 1141–1143, Dr. G. Schröder, "x) von Acryl–Verbindungen, $x_1$) von Acrylsäuren bzw. Deren Estern, Allgemeines".

J. Phys., 100, (month unavailable) 1996, pp. 17766–17771, L. S. Sapochak et al, "Systematic Study of the Photoluminescent and Electroluminescent Properties of Pentacoodinate Carboxylate and Chloro Bis(8–hydroxyquinaldine) Complexes of Gallium(III)".

Z. Naturforsch, 46b, (month unavailable) 1991, p. 1065, H. Schmidbaur et al, "Modellsysteme für die Gallium–Extraktion, II Synthese und Struktur von Bis(oxinato)gallium(III)–Carboxylaten".

* cited by examiner

ELECTROLUMINESCENT SYSTEMS WITH POLYNULCEAR METAL COMPLEXES

This application is the National stage Application of PCT/E99/06124, which claims a priority from German Application 183 39 946.4 filed Sep. 2, 1988.

An electroluminescent (EL) assembly is characterized in that it emits light and current flows when an electric potential is applied. Such assemblies have long been known in industry under the name "light emitting diodes". The emission of light results from positive charges (holes) and negative charges (electrons) recombining with emission of light.

In the development of light-emitting components for electronics or optics, use is at present mainly made of inorganic semiconductors such as gallium arsenide. Dot-shaped display elements can be produced on the basis of such substances. Large-area assemblies are not possible.

Apart from the semiconductor light emitting diodes, electroluminescent assemblies based on vapour-deposited low molecular weight organic compounds are known (U.S. Pat. No. 4,539,507, U.S. Pat. No. 4,769,262, U.S. Pat. No. 5,077,142, EP-A 0 406 762, EP-A 0 278 758, EP-A 0 278 757).

Furthermore, polymers such as poly-(p-phenylenes) and poly-(p-phenylene-vinylenes) (PPV)) have been described as electroluminescent polymers: G. Leising et al., Adv. Mater. 4 (1992) No. 1; Friend et al., J. Chem. Soc., Chem. Commun. 32 (1992); Saito et al., Polymer, 1990, Vol. 31, 1137; Friend et al., Physical Review B, Vol. 42, No. 18, 11670 or WO-A 90/13148. Further examples of PPVs in electroluminescence displays are described in EP-A 0 443 861, WO-A 92/03490 and 92/03491.

EP-A 0 294 061 discloses an optical modulator based on polyacetylene.

To produce flexible polymer LEDs, Heeger et al. have proposed soluble conjugated PPV derivatives (WO-A 92/16023).

Polymer blends of different compositions are likewise known: M. Stolka et al., Pure & Appt. Chem., Vol. 67, No. 1, pp 175–182, 1995; H. Bassler et al., Adv. Mater. 1995, 7, No. 6, 551; K. Nagai et al., Appl. Phys. Lett. 67 (16), 1995, 2281; EP-A 0 532 798.

The organic EL assemblies generally contain one or more layers of organic charge transport compounds. The in-principle structure in the order of the layers is as follows:

1 support, substrate
2 base electrode
3 hole injection layer
4 hole transport layer
5 light-emitting layer
6 electron transport layer
7 electron injection layer
8 top electrode
9 contacts
10 sheathing, encapsulation.

The layers 3 to 7 represent the electroluminescent element.

This structure represents the most general case and can be simplified by leaving out individual layers so that one layer takes on a plurality of functions. In the simplest case, an EL assembly consists of two electrodes between which there is located an organic layer which fulfils all functions including the emission of light. Such systems are described, for example, in the Application WO-A 90/13148 on the basis of poly-(p-phenylene-vinylene).

Multilayer systems can be built up by vapour deposition methods in which the layers are applied successively from the gas phase or by means of casting processes. Owing to the higher process speeds, casting processes are preferred. However, partial dissolution of a layer which has already been applied when the next layer is applied on top can present a difficulty in certain cases.

It is an object of the present invention to provide electroluminescent assemblies having a high light flux in which novel metal complexes having improved solubility in customary solvents are used as emitters and/or electron conductors. These novel metal complexes should also be able to be applied by vapour deposition from the gas phase.

It has been found that electroluminescent assemblies containing the metal complexes specified below meet these requirements. In the following, the term zone is equivalent to the term layer.

DESCRIPTION

The present invention accordingly provides an electroluminescent assembly comprising a substrate, an anode, an electroluminescent element and a cathode, where at least one of the two electrodes is transparent in the visible spectral region and the electroluminescent element comprises one or more zones selected from the group consisting of a hole injection zone, a hole transport zone, an electroluminescent zone, an electron transport zone and an electron injection zone in the specified order, where each of the zones present may also assume functions of the other zones mentioned, characterized in that the electroluminescent element contains a multinuclear metal complex.

The hole injection zone preferably contains an uncharged or cationic polythiophene of the formula (I)

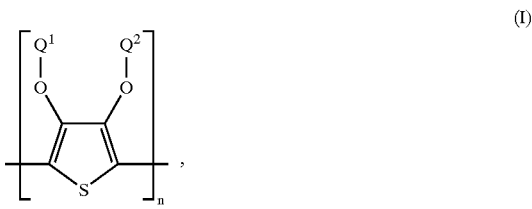

(I)

where $Q^1$ and $Q^2$ represent, independently of one another, hydrogen, substituted or unsubstituted $(C_1-C_{20})$-alkyl, $CH_2OH$ or $(C_6-C_{14})$-aryl or $Q^1$ and $Q^2$ together represent $-(CH_2)_m-CH_2-$ where m=0 to 12, preferably from 1 to 5, or $(C_6-C_{14})$-arylene, and n represents an integer from 2 to 10,000, preferably from 5 to 5000.

The hole conductor zone adjoining the hole injection zone preferably contains one or more aromatic tertiary amino compounds, preferably substituted or unsubstituted triphenylamine compounds, particularly preferably 1,3,5-tris (aminophenyl)benzene compounds of the formula (II).

The zones or zone located between the hole injection zone and the cathode can also assume a plurality of functions, i.e. one zone can comprise, for example, hole-injecting, hole-transporting, electroluminescent, electron-transporting and/or electron-injecting substances.

The electroluminescent element can additionally contain one or more transparent polymeric binders.

The substituted or unsubstituted 1,3,5-tris(aminophenyl) benzene compound preferably represents an aromatic tertiary amino compound of the general formula (II)

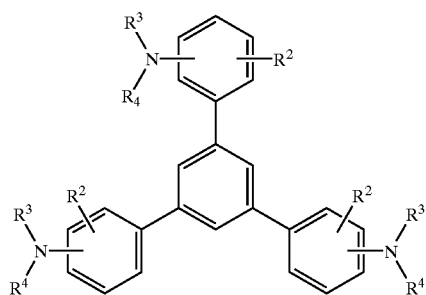

(II)

in which
  $R^2$ represents hydrogen, substituted or unsubstituted alkyl or halogen,
  $R^3$ and $R^4$ represent, independently of one another, substituted or unsubstituted $(C_1-C_{10})$-alkyl, alkoxycarbonyl-substituted $(C_1-C_{10})$-alkyl or substituted or unsubstituted aryl, aralkyl or cycloalkyl.

$R^3$ and $R^4$ preferably represent, independently of one another, $(C_1-C_6)$-alkyl, in particular methyl, ethyl, n- or iso-propyl, n-, iso-, sec or tert-butyl, $(C_1-C_4)$-alkoxcarbonyl-$(C_1-C_6)$-alkyl such as methoxycarbonyl-, ethoxycarbonyl-, propoxycarbonyl- or butoxycarbonyl-$(C_1-C_4)$-alkyl, or unsubstituted or $(C_1-C_4)$-alkyl- and/or $(C_1-C_4)$-alkoxy-substituted phenyl-$(C_1-C_4)$-alkyl, naphthyl-$(C_1-C_4)$-alkyl, cyclopentyl, cyclohexyl, phenyl or naphthyl.

Particularly preferably, $R^3$ and $R^4$ represent, independently of one another, unsubstituted phenyl or naphthyl or phenyl or naphthyl substituted in each case by from 1 to 3 methyl, ethyl, n-, iso-propyl, methoxy, ethoxy, n- and/or iso-propoxy groups.

$R^2$ preferably represents hydrogen, $(C_1-C_6)$-alkyl, for example methyl, ethyl, n- or iso-propyl, n-, iso-, sec- or tert-butyl, or chlorine.

Such compounds and their preparation are described in U.S. Pat. No. 4,923,774 for use in electrophotography, which patent is hereby expressly incorporated by reference into the present description. The tris-nitrophenyl compound can be converted into the tris-aminophenyl compound by, for example, generally known catalytic hydrogenation, for example in the presence of Raney nickel ((Houben-Weyl 4/1C, 14–102, Ullmann (4) 13, 135–148). The amino compound is reacted with substituted halogenobenzenes in a generally known manner.

As examples, mention may be made of the following compounds:

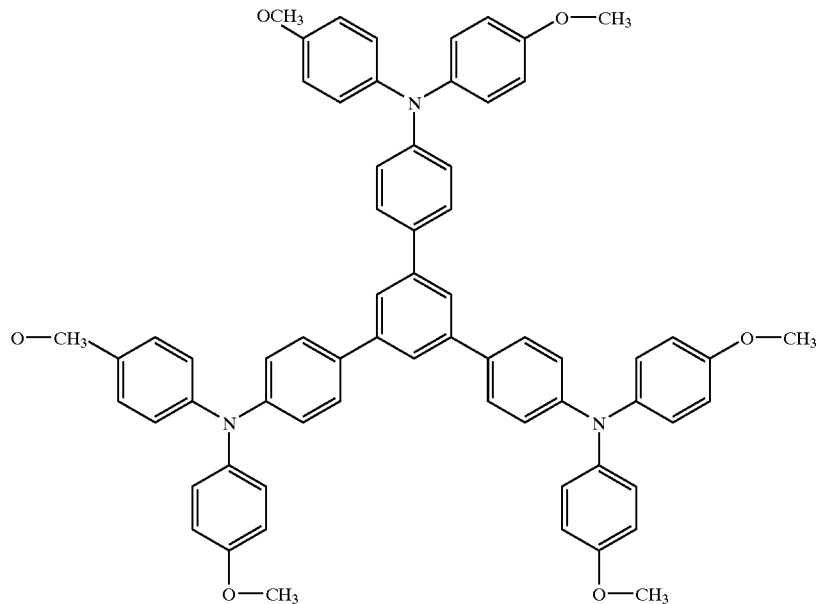

A1

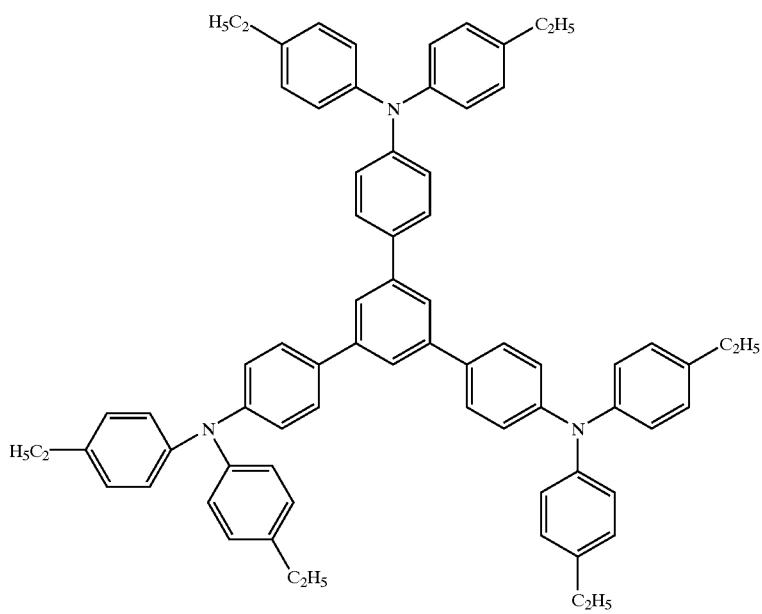

A2

Apart from the tertiary amino compound, it is possible, if desired, to use further hole conductors, for example in the form of a mixture with the tertiary amino compound, for building up the electroluminescent element. It is possible here to use either one or more compounds of the formula (II), with mixtures of isomers also being included, or else mixtures of hole transport compounds with compounds of tertiary amino compounds having the general formula (II) and different structures.

A listing of possible hole injection materials and hole conductor materials is given in EP-A 0 532 798.

In the case of mixtures of the aromatic amines, the compounds can be used in any ratio.

Examples which may be mentioned are:

Materials which have hole-conducting properties and can be used in pure form or as components of mixtures with the tertiary amino compounds are, for example, the following compounds, where $X^1$ to $X^6$ represent, independently of one another, H, halogen, alkyl, aryl, alkoxy, aryloxy.

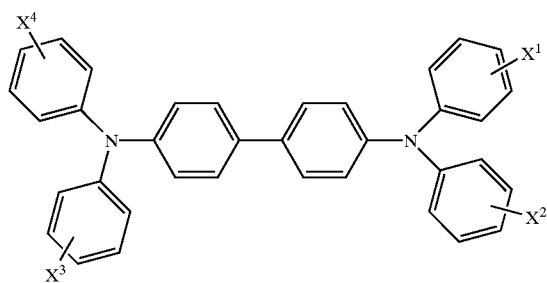

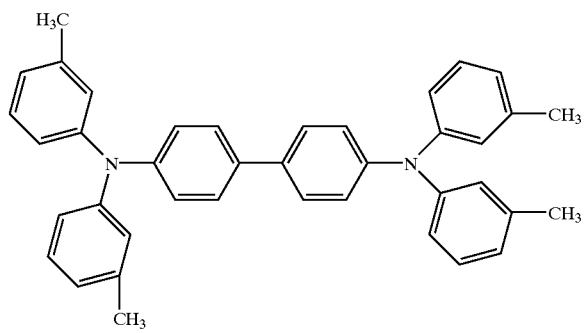

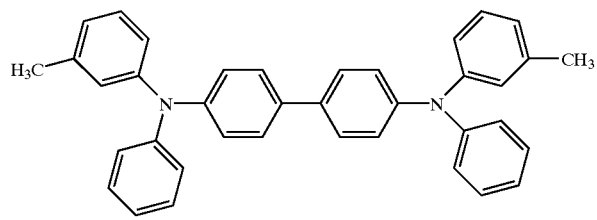

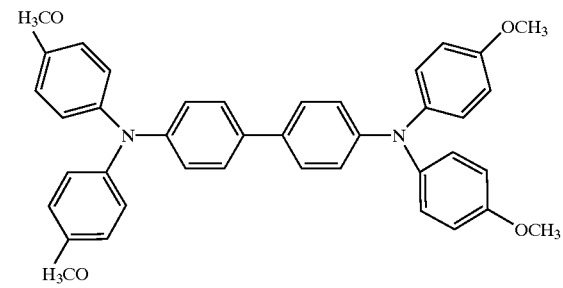

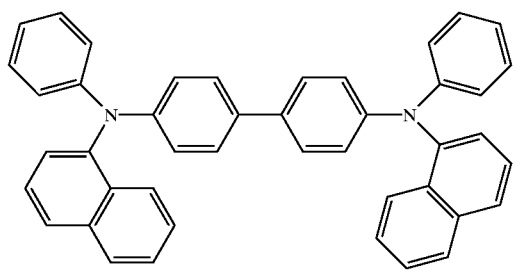
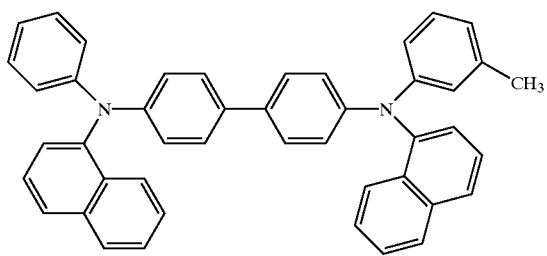
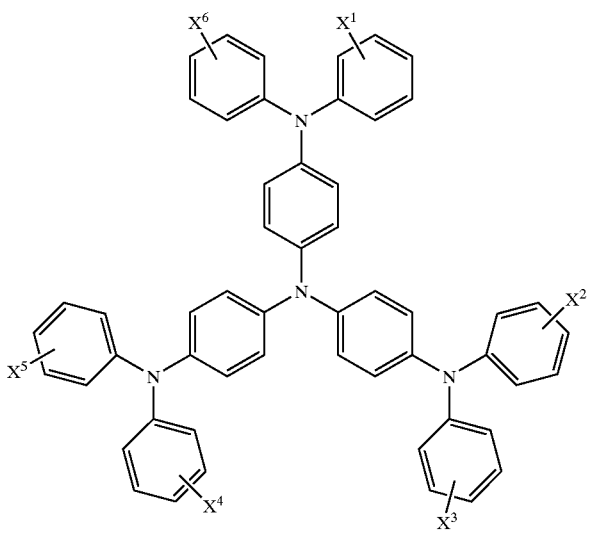
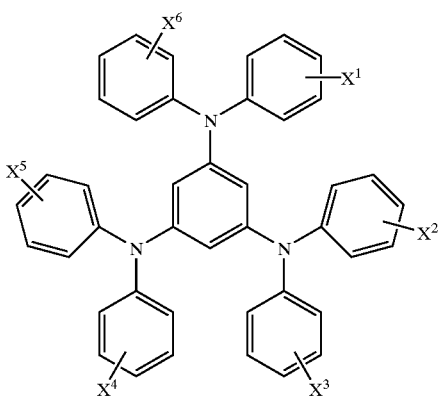
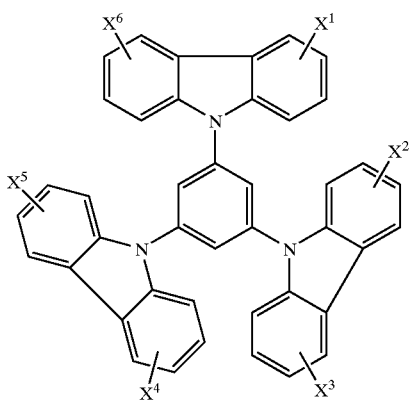
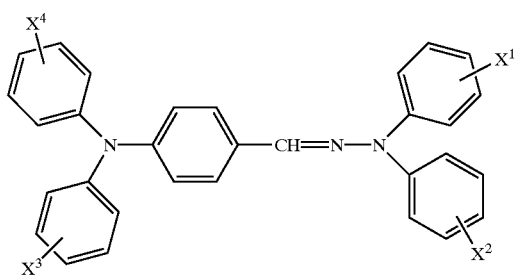
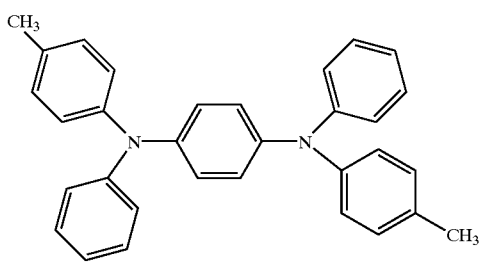
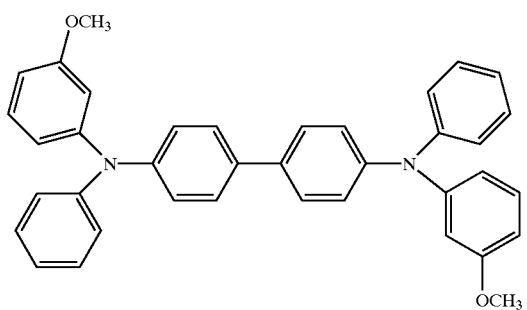

-continued
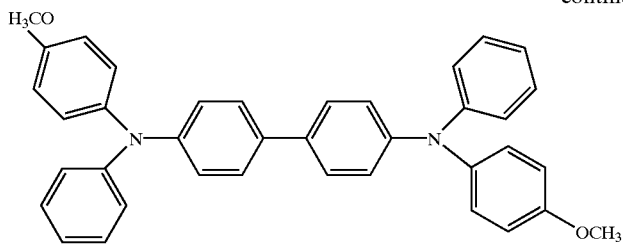
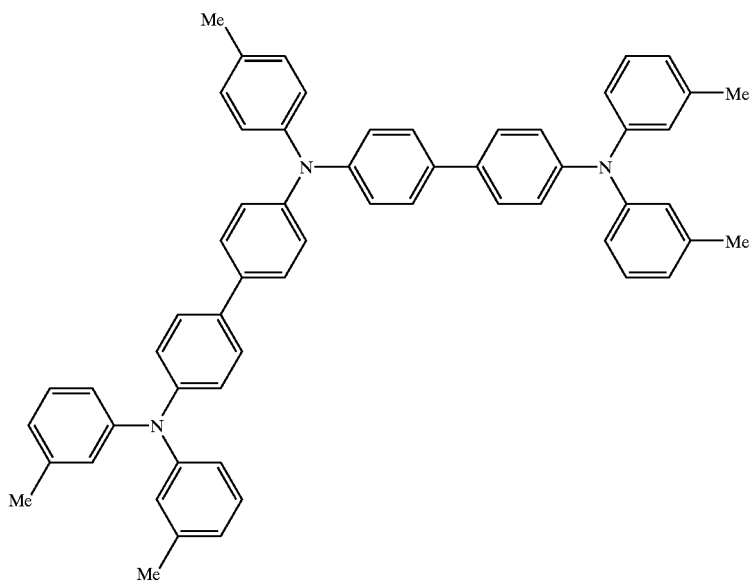
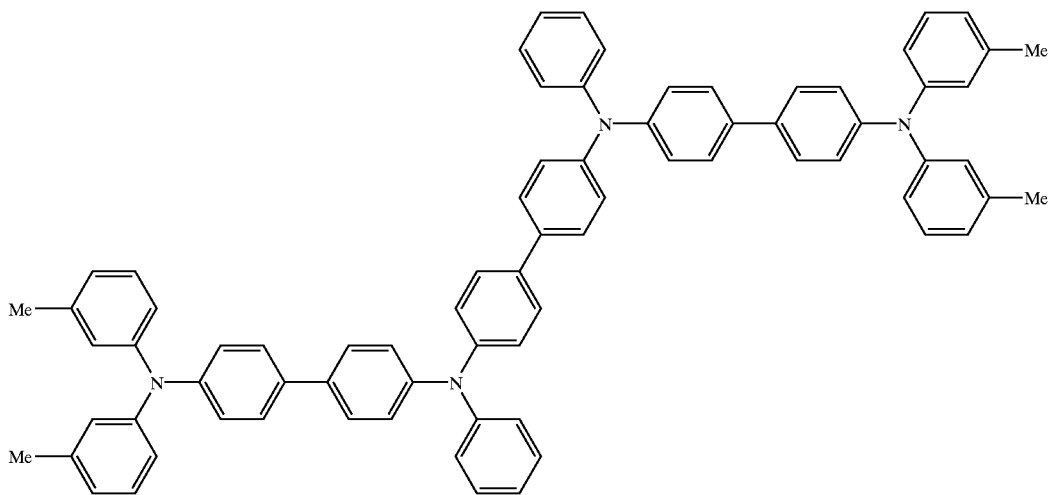
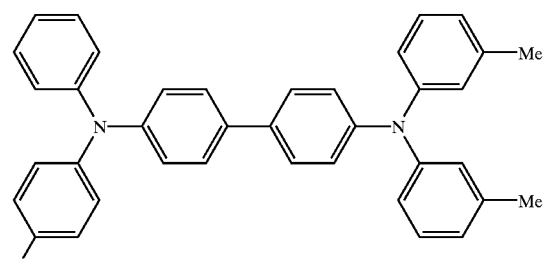

-continued

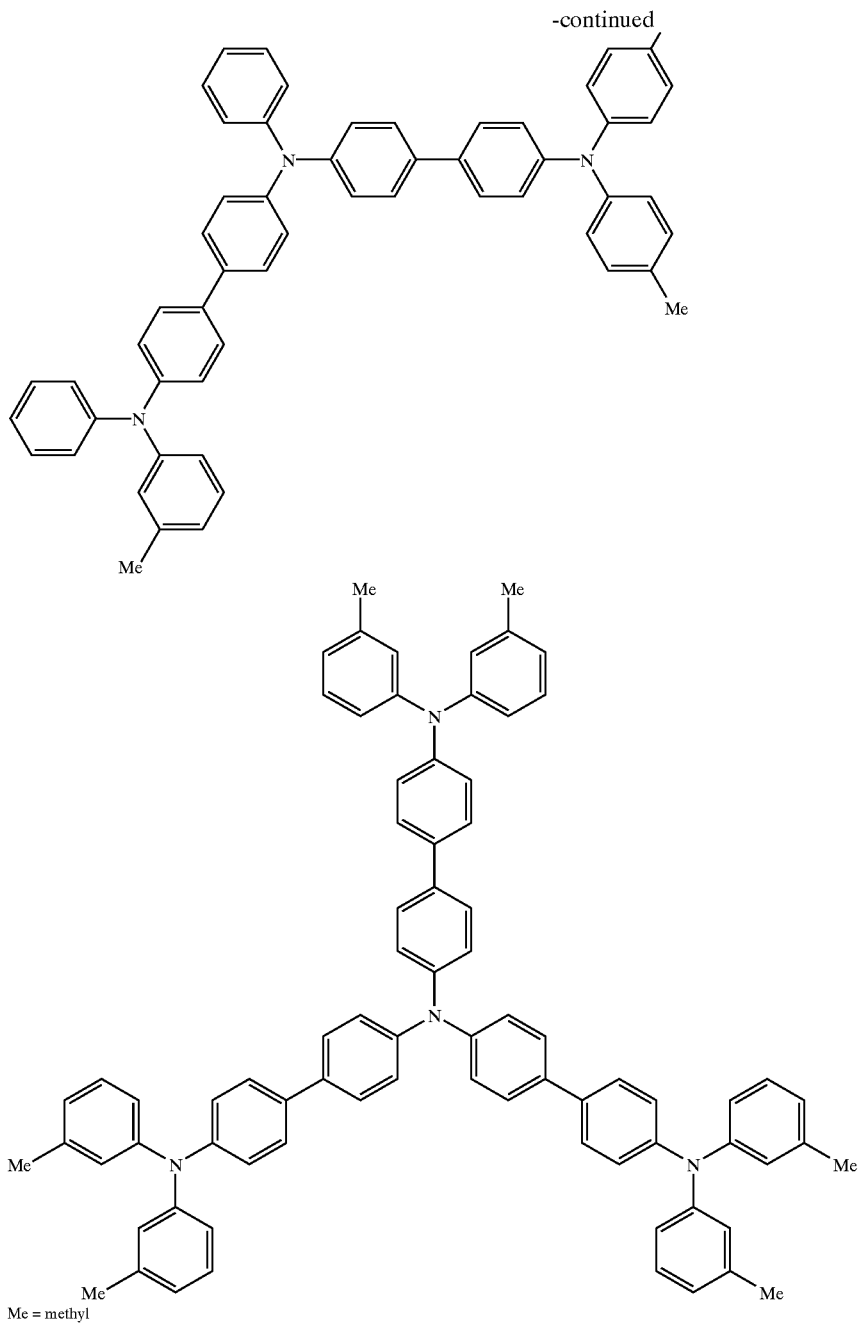

Me = methyl

These and further examples are described in J. Phys. Chem. 1993, 97, 6240–6248 and Appl. Phys. Lett., Vol. 66, No. 20, 2679–2681.

In general, various amines having different basic structures and/or different substitution patterns can be mixed.

$X^1$ to $X^6$ preferably represent, independently of one another, hydrogen, fluorine, chlorine, bromine, $(C_1–C_{10})$-, in particular $(C_1–C_4)$-alkyl or -alkoxy, phenyl, naphthyl, phenoxy and/or naphthyloxy. The aromatic rings may be monosubstituted, disubstituted, trisubstituted or tetrasubstituted by identical or different radicals $X^1$ to $X^6$.

The polythiophenes of the structural repeating unit of the formula (I) are known (cf. EP-A 0 440 958 and 0 339 340). The preparation of the dispersions or solutions used according to the invention is described in EP-A 0 440 957 and DE-A 42 11 459.

The polythiophenes in the dispersion or solution are preferably used in cationic form as is obtained, for example, by treatment of the uncharged thiophenes with oxidants. Customary oxidants such as potassium peroxodisulphate are used for the oxidation. As a result of the oxidation, the polythiophenes acquire positive charges which are not shown in the formulae since their number and their position cannot be determined unambiguously. They can be prepared directly on supports as described in EP-A 0 339 340.

$Q^1$ and $Q^2$ in formula (I) preferably represent —$(CH_2)_m$—$CH_2$— where m=1 to 4, very particularly preferably ethylene.

Preferred cationic or uncharged polydioxythiophenes comprise structural units of the formula (Ia) or (Ib)

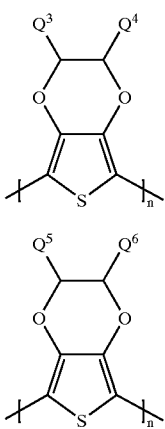

(Ia)

(Ib)

where
- $Q^3$ and $Q^4$ represent, independently of one another, hydrogen, substituted or unsubstituted $(C_1-C_{18})$-alkyl, preferably $(C_1-C_{10})$-, in particular $(C_1-C_6)$-alkyl, $(C_2-C_{12})$-alkenyl, preferably $(C_2-C_8)$-alkenyl, $(C_3-C_7)$-cycloalkyl, preferably cyclopentyl, cyclohexyl, $(C_7-C_{15})$-aralkyl, preferably phenyl-$(C_1-C_4)$-alkyl, $(C_6-C_{10})$-aryl, preferably phenyl, naphthyl, $(C_1-C_{18})$-alkoxy, preferably $(C_1-C_{10})$-alkoxy, for example methoxy, ethoxy, n-or iso-propoxy, or $(C_2-C_{18})$-alkyloxy ester and
- $Q^5$ and $Q^6$ represent, independently of one another, hydrogen or $(C_1-C_{18})$-alkyl, preferably $(C_1-C_{10})$-, in particular $(C_1-C_6)$-alkyl, $(C_2-C_{12})$-alkenyl, preferably $(C_2-C_8)$-alkenyl, $(C_3-C_7)$-cycloalkyl, preferably cyclopentyl, cyclohexyl, $(C_7-C_{15})$-aralkyl, preferably phenyl-$(C_1-C_4)$-alkyl, $(C_6-C_{10})$-aryl, preferably phenyl, naphthyl, $(C_1-C_{18})$-alkoxy, preferably $(C_1-C_{10})$-alkoxy, for example methoxy, ethoxy, n-or iso-propoxy, or $(C_2-C_{18})$-alkyloxy ester which are each substituted by at least one sulphonate group, where, if $Q^5$ represents hydrogen, $Q^6$ is not hydrogen and vice versa,
- n represents an integer from 2 to 10,000, preferably from 5 to 5000.

Particular preference is given to cationic or uncharged polythiophenes of the formulae (Ia-1) and (Ib-1)

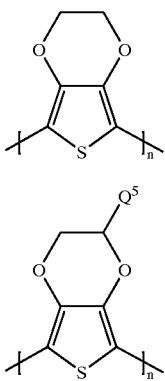

(Ia-1)

(Ib-1)

where
$Q^5$ and n are as defined above.

To compensate the positive charge, the cationic form of the polythiophenes contains anions, preferably polyanions.

Polyanions present are preferably the anions of polymeric carboxylic acids such as polyacrylic acids, polymethacrylic acid or polymaleic acids and polymeric sulphonic acids such as polystyrenesulphonic acids and polyvinylsulphonic acids. These polycarboxylic and polysulphonic acids can also be copolymers of vinylcarboxylic and vinylsulphonic acids with other polymerizable monomers such as acrylic esters and styrene.

The counterion is particularly preferably the anion of polystyrenesulphonic acid.

The molecular weight of the polyacids on which the polyanions are based is preferably from 1000 to 2,000,000, particularly preferably from 2000 to 500,000. The polyacids or their alkali metal salts are commercially available, for example polystyrenesulphonic acids and polyacrylic acids, or else can be prepared by known methods (see, for example, Houben-Weyl, Methoden der organischen Chemie, volume E 20 Makromolekulare Stoffe, part 2 (1987), p. 1141 ff).

In place of the free polyacids required for forming the dispersions of polydioxythiophenes and polyanions, it is also possible to use mixtures of alkali metal salts of the polyacids and corresponding amounts of monoacids.

In the case of the formulae (Ib) and (Ib-1), the polydioxythiophenes bear positive and negative charges in the monomer unit itself.

The assemblies of the invention may, if desired, contain polymers and/or copolymers as binders, for example polycarbonates, polyester carbonates, copolymers of styrene such as SAN or styrene acrylates, polysulphones, polymers based on vinyl-containing monomers, for example poly (meth)acrylates, polyvinylpyrrolidone, polyvinylcarbazole, vinyl acetate and vinyl alcohol polymers and copolymers, polyolefins, cyclic olefin copolymers, phenoxy resins, etc. It is also possible to use mixtures of various polymers. The polymeric binders have molecular weights of from 10,000 to 2,000,00 g/mol, are soluble and film-forming and are transparent in the visible spectral region. They are described, for example, in Encyclopedia of Polymer Science and Engineering, 2nd Ed., a Wiley-Interscience publication. They are usually used in an amount of up to 95% by weight, preferably up to 80% by weight, based on the total weight of the electroluminescent elements.

The multinuclear metal complex is preferably a compound of the general formula (III)a, (III)b or (III)c

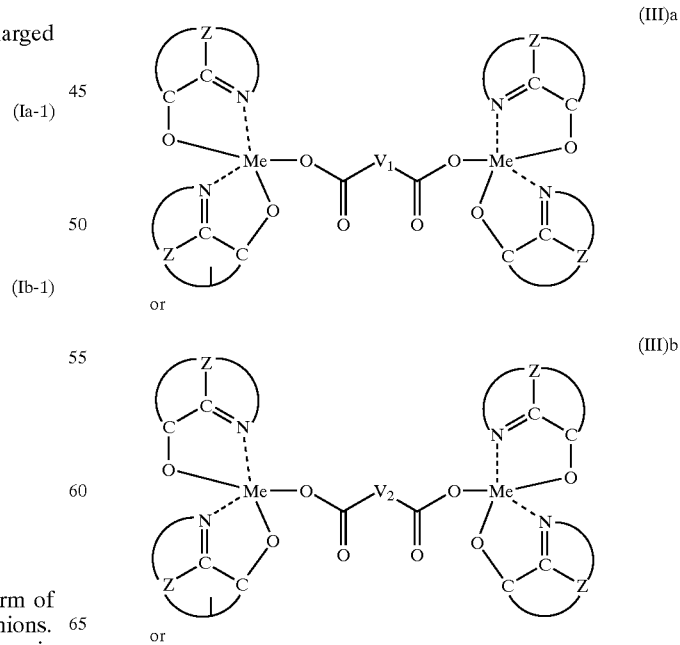

-continued (III)c

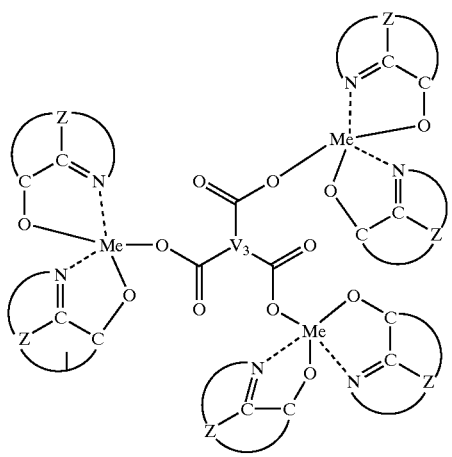

where
- Me represents a metal,
- $V_1$ represents a substituted or unsubstituted and/or branched or unbranched alkylene radical, cycloalkylene radical or poly(oxyalkylene) radical such as $-(CH_2-O)_n-$, $-(CH_2-CH_2-O)_n-$ where n=1 to 1000,
- $V_2$ represents a substituted or unsubstituted and/or branched or unbranched alkenylene radical or alkinylene radical
- $V_3$ represents a substituted or unsubstituted and/or branched or unbranched alkylene radical or cycloalkylene radical, and
- Z represents atoms which complete a moiety which comprises at least 2 fused rings.

It is generally possible to utilize trivalent metals which are known to form chelates.

The metal can be aluminium, gallium, indium or a lanthanide.

Z completes a heterocyclic moiety which comprises at least two fused rings of which one is an azole or azine ring; further additional aliphatic or aromatic rings may be bound to the two fused rings.

The component particularly preferably represents a compound of the general formula (III)d, (III)e or (III)f (III)d

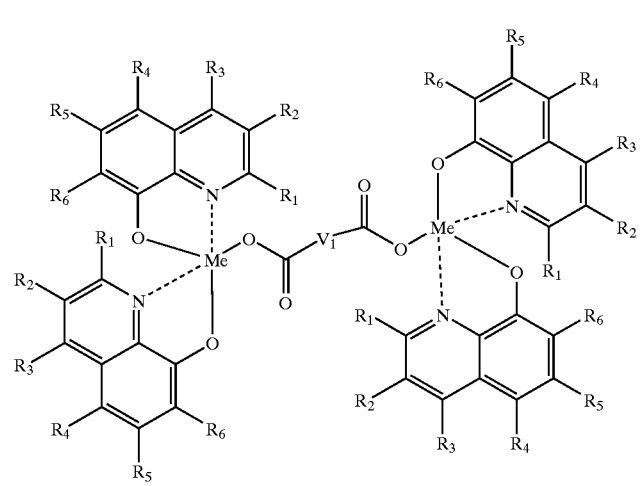

or (III)e

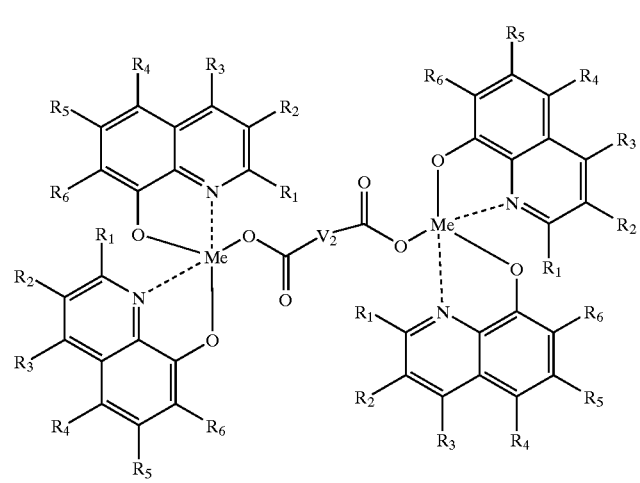

or

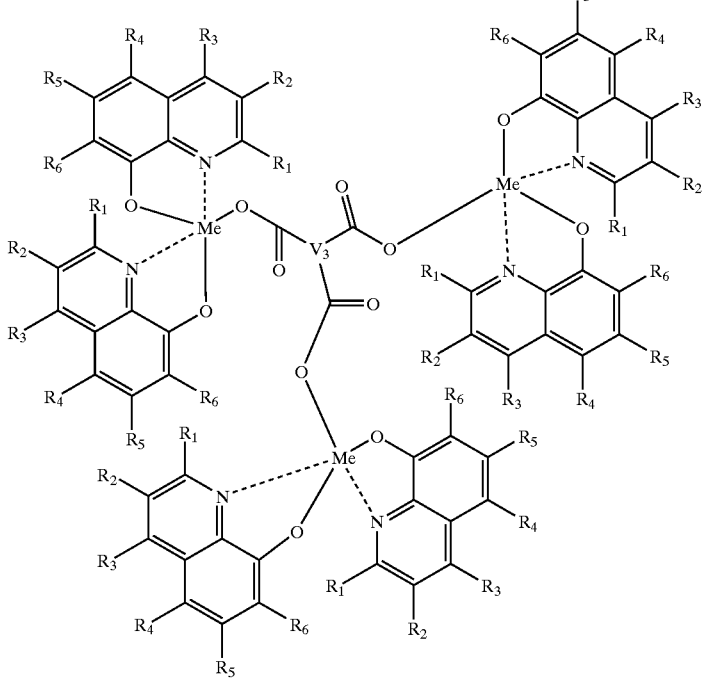

in which

R₁ particularly preferably represents $(C_1-C_{16})$-alkyl, and

R₂, R₃, R₄, R₅, R₆ represent, independently of one another, hydrogen or substituted or unsubstituted $(C_1-C_{16})$-alkyl or acyl or halogen or substituted or unsubstituted aryl or cyano or sulphonamido or a substituted or unsubstituted amino group and Me particularly preferably represents Al, Ga, or In.

The multinuclear metal complex is very particularly preferably a compound of the general formula (III)d, (III)e or (III)f in which R₁ very particularly preferably represents $(C_1-C_{10})$-alkyl and R₂, R₃, R₄, R₅, R₆ very particularly preferably represent, independently of one another, hydrogen, substituted or unsubstituted $(C_1-C_{10})$-alkyl or acyl or sulphonamido and Me very particularly preferably represents Al, Ga and V₁ very particularly preferably represents a branched or unbranched $(C_1-C_{10})$-alkylene radical which may be unsubstituted or substituted by a thiophene unit, and V₂ very particularly preferably represents a branched or unbranched $(C_1-C_{10})$-alkylene or alkinylene radical and V₃ very particularly preferably represents a branched $(C_1-C_{10})$-alkylene radical.

Examples which may be mentioned are:

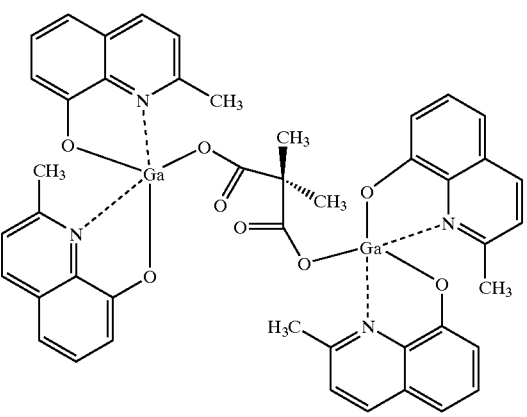

B1

B2
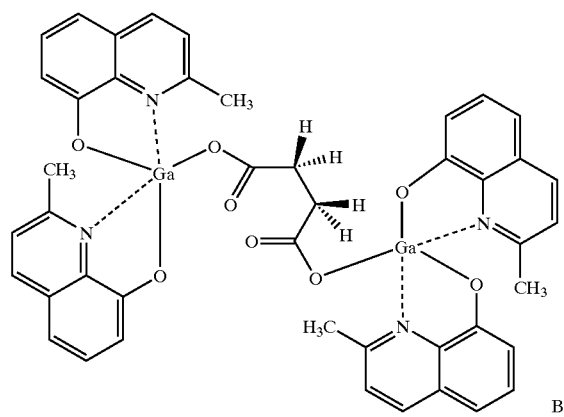
B3
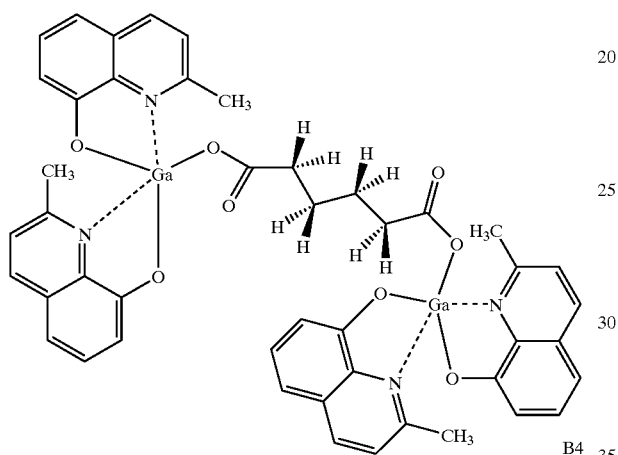
B4
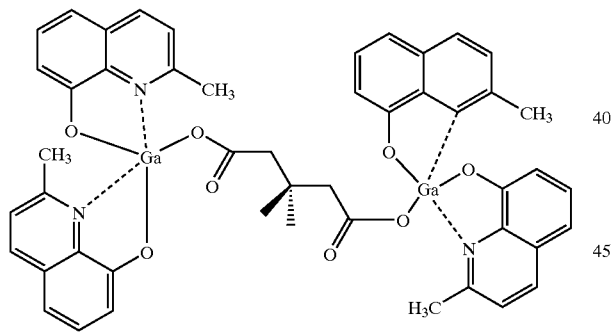
B5
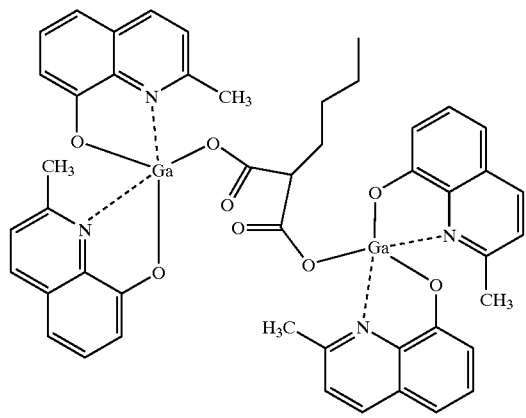
B6
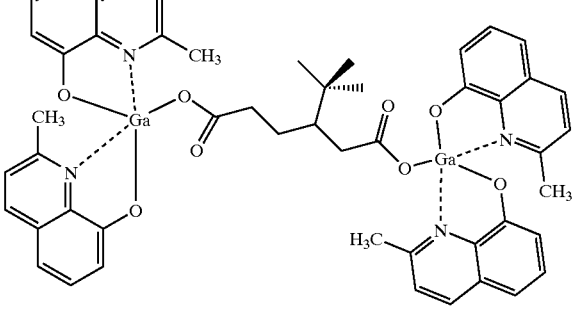
B7
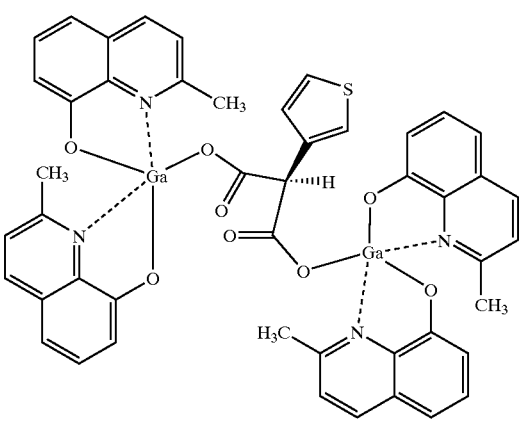
B8
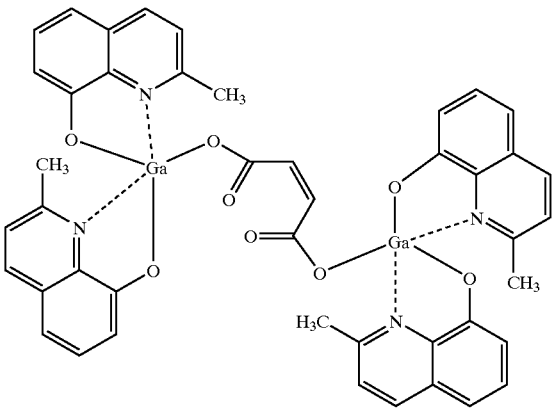
B9
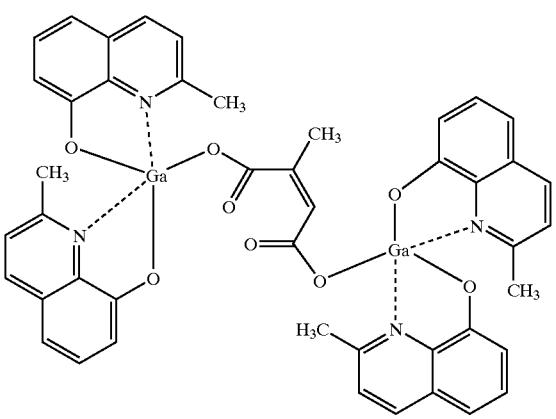

-continued

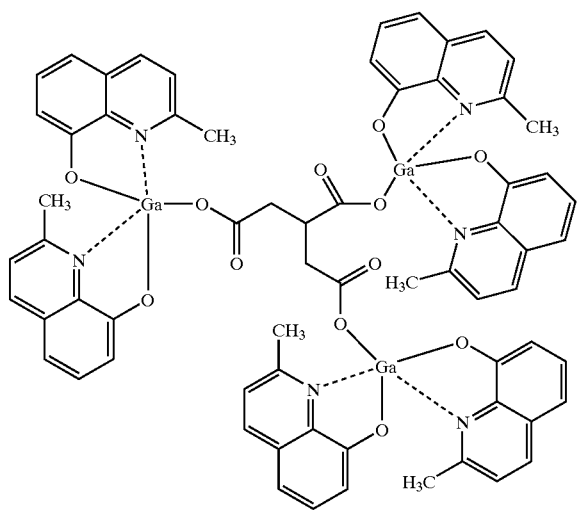

B10

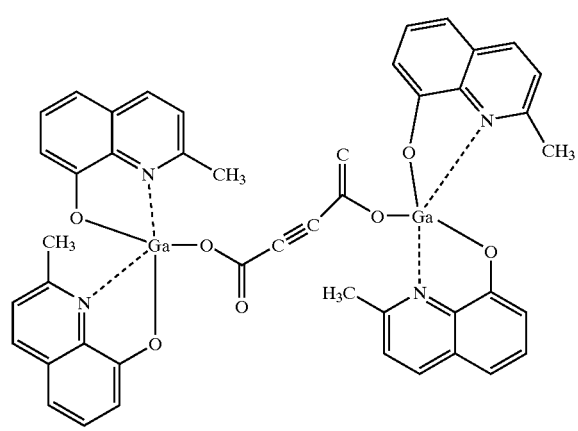

B11

It is possible to use one or more compounds of the formulae B1 to B11.

Some of the 8-hydroxyquinoline ligands are commercially available or they can be prepared by known methods of organic chemistry (R. G. W. Hallingshead, Vol.1, Chap.6, Butterworths, London (1954)). The metal complexes can likewise be prepared by known methods (L. S. Sopachak et al., J. Phys. Chem. 100, 177 766 (1996) and H. Schmidbaur et al., Z. Naturforsch. 46b, 1065 (1991).

Multinuclear metal complexes containing units derived from aryl compounds are described in EP-A 0579 151.

To produce the electroluminescent element, the multinuclear metal complex and, if desired, the tertiary amino compound and the binder are dissolved in a suitable solvent and applied to a suitable substrate by casting, doctor blade coating or spin coating. However, the metal complex can be applied, if desired, as a separate layer by a vapour deposition process. The substrate can be, for example, glass or a plastic material which is provided with a transparent electrode. As plastic material, it is possible to use, for example, a film of polycarbonate, polyester such as polyethylene terephthalate or polyethylene naphthalate, polysulphone or polyimide. Suitable transparent electrodes are a) metal oxides, for example indium-tin oxide (ITO), tin oxide (NESA), zinc oxide, doped tin oxide, doped zinc oxide, etc., b) semitransparent metal films, for example Au, Pt, Ag, Cu etc., c) conductive polymer films such as polyanilines, polythiophenes, etc.

The metal oxide electrodes and the semitransparent metal film electrodes are applied in a thin layer by techniques such as vapour deposition, sputtering, platination, etc. The conductive polymer films are applied from the solution by techniques such as spin coating, casting, doctor blade coating, etc.

The thickness of the transparent electrodes is from 3 nm to a number of $\mu$m, preferably from 10 nm to 500 nm.

The electroluminescent layer is applied as a thin film directly to the transparent electrode or to any charge transport layer which is present. The thickness of the film is from 10 to 500 nm, preferably from 20 to 400 nm, particularly preferably from 50 to 250 nm.

A further charge transport layer can be inserted on the electroluminescent layer before a counterelectrode is applied.

A listing of suitable charge-transporting intermediate layers, which may be hole conductor and/or electron conductor materials and may be present in polymeric or low molecular weight form, if desired as a blend, is given in EP-A 0 532 798. Particularly suitable materials are specifically substituted polythiophenes which have hole transport properties. They are described, for example, in EP-A 0 686 662.

The content of low molecular weight hole conductor in a polymeric binder can be varied in the range from 2 to 97% by weight; the content is preferably from 5 to 95% by weight, particularly preferably from 10 to 90% by weight, in particular from 10 to 85% by weight. The hole injection or hole conduction zones can be deposited using various methods.

Film-forming hole conductors can also be used in pure form (100% pure). If desired, the hole injection or hole conduction zone may also contain proportions of an electroluminescent substance.

Blends which consist exclusively of low molecular weight compounds can be vapour-deposited; soluble and film-forming blends which may contain a binder in addition to low molecular weight compounds can be deposited from a solution, for example by means of spin coating, casting or doctor blade coating.

It is also possible to apply emitting and/or electron-conducting substances in a separate layer on the hole conduction layer. Here, an emitting substance can also be added as dopant to the layer containing the compound (II) and an electron-conducting substance can be applied in addition. An electroluminescent substance can also be added to the electron injection or electron conduction layer.

The content of low molecular weight electron conductors in the polymeric binder can be varied in the range from 2 to 95% by weight; the content is preferably from 5 to 90% by weight, particularly preferably from 10 to 85% by weight. Film-forming electron conductors can also be used in pure form (100% pure).

The counterelectrode comprises a conductive substance which may be transparent. Preference is given to metals, for example Al, Au, Ag, Mg, In, etc. or alloys and oxides of these which can be applied by techniques such as vapour deposition, sputtering and platination.

The assembly of the invention is brought into contact with the two electrodes by means of two electric leads (for example metal wires).

On application of a DC potential of from 0.1 to 100 volts, the assemblies emit light having a wavelength of from 200 to 2000 nm. They display photoluminescence in the range from 200 to 2000 nm.

The assemblies of the invention are suitable for producing units for lighting and for display of information.

The invention is further described in the following illustrative examples in which all parts and percentages are by weight unless otherwise indicated.

EXAMPLES

Example 1

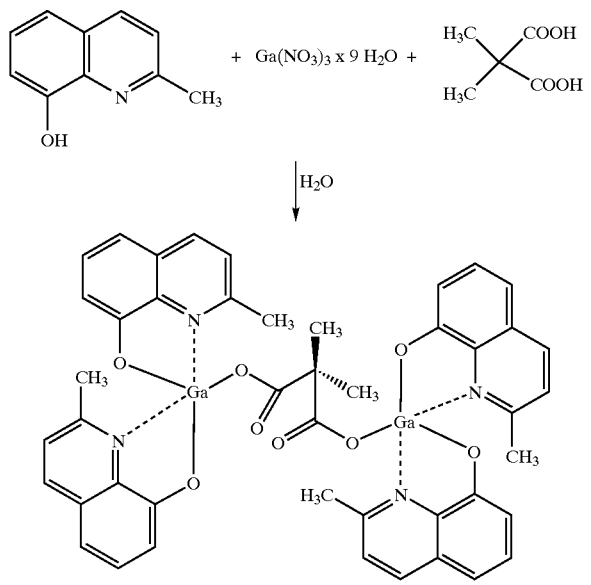

A solution of 1.0 g (6.3 mmol) of recrystallized 8-hydroxyquinoline and 5.0 g (38.4 mmol) of dimethylmalonic acid in 750 ml of distilled water is added dropwise to a solution of 1.67 g (4 mmol) of gallium(III) nitrate hydrate in 250 ml of distilled water. The product can be precipitated at pH 4 to 5 by addition of concentrated ammonia. The precipitate is separated off and washed with water. Drying gives a light-yellow crystalline solid which has a yellowish green fluorescence.

Yield: 1.12 g (1.2 mmol≙62% of theory).

Example 2

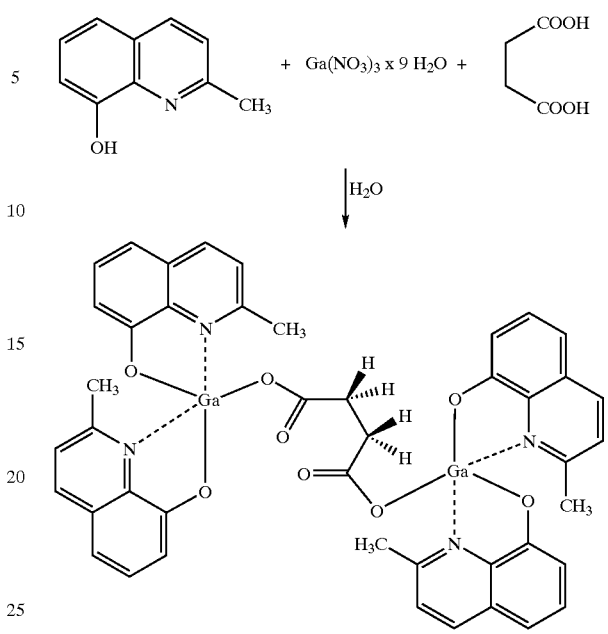

A solution of 0.28 g (1.76 mmol) of recrystallized 8-hydroxyquinaldine and 10.0 g (84.6 mmol) of succinic acid in 1000 ml of distilled water is added dropwise to a solution of 0.37 g (0.89 mmol) of gallium(III) nitrate hydrate in 100 ml of distilled water. The product can be precipitated at pH 4 to 5 by addition of concentrated ammonia. The precipitate is separated off and washed with water. Drying gives a light-yellow crystalline solid which has a greenish blue fluorescence.

Yield: 0.12 g (0.13 mmol≙30.7% of theory).

Example 3

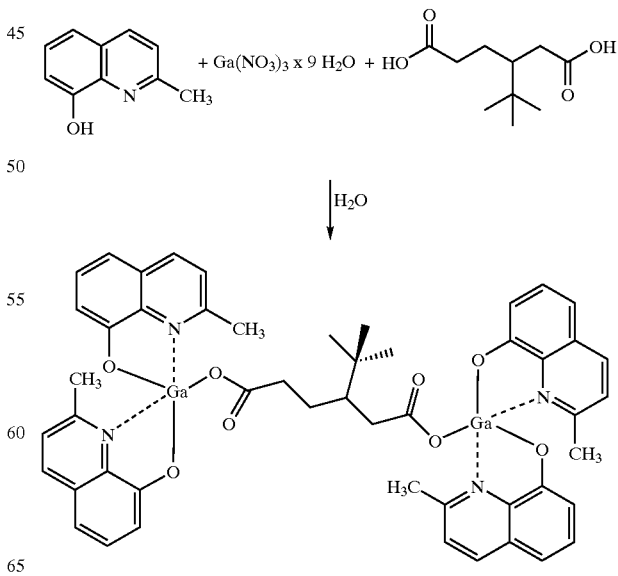

A solution of 0.32 g (2.0 mmol) of recrystallized 8-hydroxyquinaldine and 2.02 g (10 mmol) of 3-tert-butyladipic acid in 100 ml of distilled water is added dropwise to a solution of 0.42 g (1.0 mmol) of gallium(III) nitrate hydrate in 60 ml of distilled water. The product can be precipitated at pH 4 to 5 by addition of concentrated ammonia. The precipitate is separated off and washed with water. Drying gives a light-yellow crystalline solid which has a yellowish green fluorescence.

Yield: 0.45 g (0.46 mmol=92% of theory).

Example 4

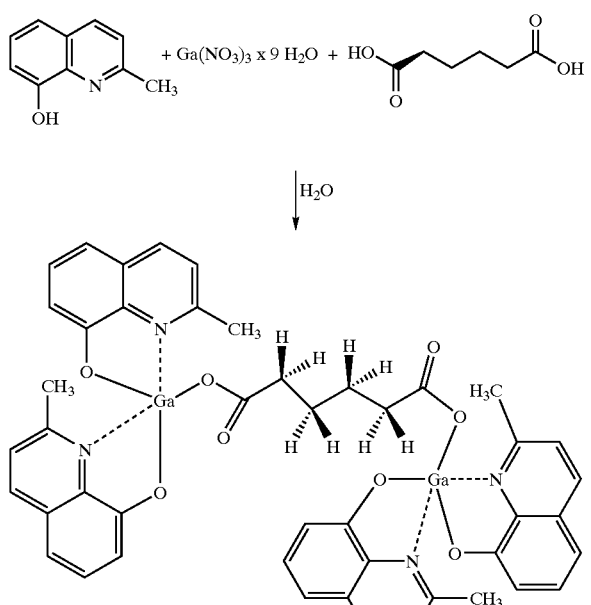

A solution of 0.28 g (1.76 mmol) of recrystallized 8-hydroxyquinaldine and 13 g (88.9 mmol) of adipic acid in 100 ml of distilled water is added dropwise to a solution of 0.37 g (0.89 mmol) of gallium(III) nitrate hydrate in 100 ml of distilled water. The product can be precipitated at pH 4 to 5 by addition of concentrated ammonia. The precipitate is separated off and washed with water. Drying gives a light-yellow crystalline solid which has a blue fluorescence.

Yield: 0.68 g (0.74 mmol=59% of theory).

Example 5

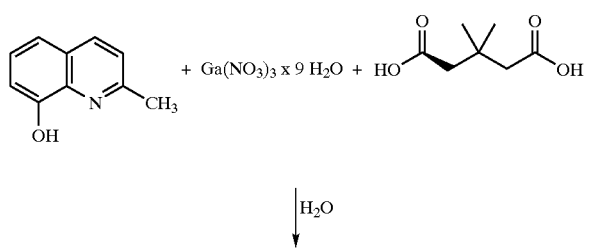

-continued

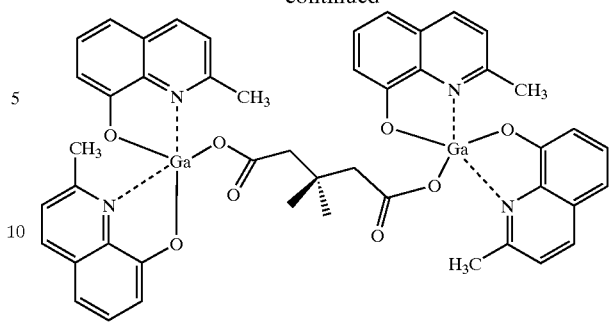

A solution of 1.27 g (8.0 mmol) of recrystallized 8-hydroxyquinaldine and 6.41 g (40 mmol) of 3,3-dimethylglutaric acid in 500 ml of distilled water is added dropwise to a solution of 1.67 g (4 mmol) of gallium(III) nitrate hydrate in 250 ml of distilled water. The product can be precipitated at pH 4 to 5 by addition of concentrated ammonia. The precipitate is separated off and washed with water. Drying gives a light-yellow crystalline solid which has a greenish blue fluorescence.

Yield: 1.70 g (1.8 mmol=90% of theory).

Example 6

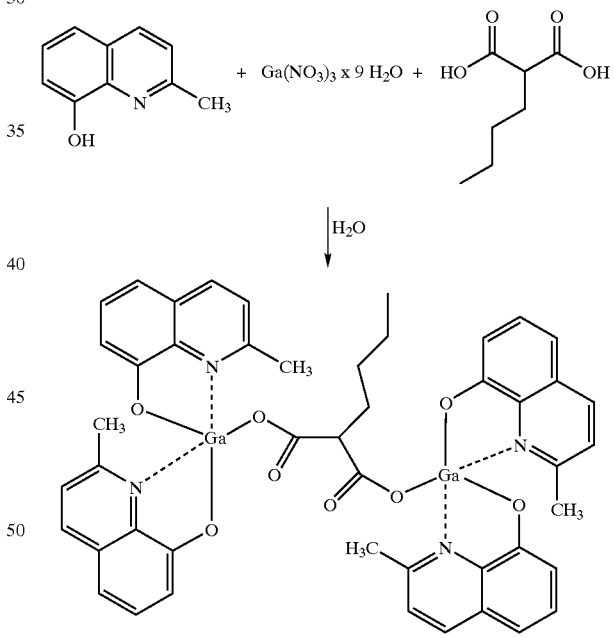

A solution of 1.27 g (8.0 mmol) of recrystallized 8-hydroxyquinaldine and 6.41 g (40 mmol) of butylmalonic acid in 250 ml of distilled water is added dropwise to a solution of 1.67 g (4 mmol) of gallium(III) nitrate hydrate in 60 ml of distilled water. The product can be precipitated at pH 4 to 5 by addition of concentrated ammonia. The precipitate is separated off and washed with water. Drying gives a light-yellow crystalline solid which has a yellowish green fluorescence.

Yield: 1.56 g (1.67 mmol=83.5% of theory).

Example 7

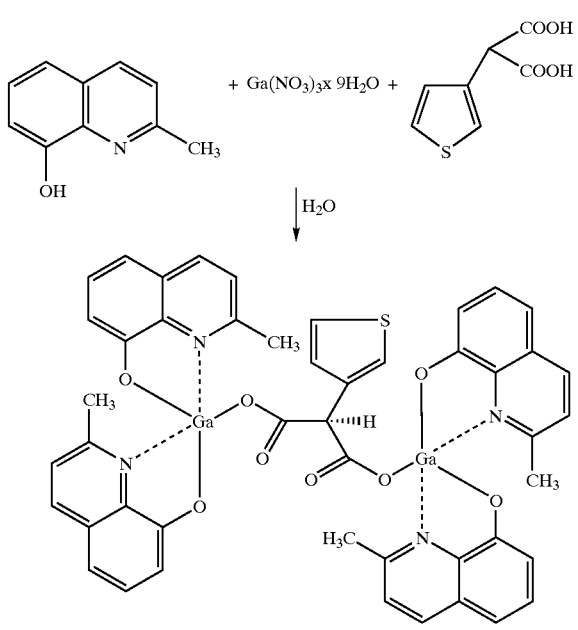

A solution of 1.27 g (8.0 mmol) of recrystallized 8-hydroxyquinaldine and 5.0 g (26.8 mmol) of 3-thienylmalonic acid in 150 ml of distilled water is added dropwise to a solution of 1.67 g (4 mmol) of gallium(III) nitrate hydrate in 150 ml of distilled water. The product can be precipitated at pH 4 to 5 by addition of concentrated ammonia. The precipitate is separated off and washed with water. Drying gives a yellow crystalline solid which has a yellowish green fluorescence.

Yield: 0.51 g (0.53 mmol≙26.5% of theory).

Example 8

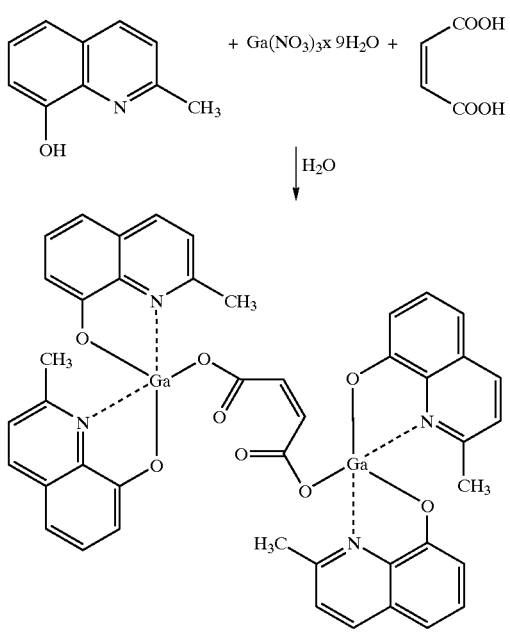

A solution of 1.4 g (8.8 mmol) of recrystallized 8-hydroxyquinaldine and 5.0 g (43.1 mmol) of maleic acid in 150 ml of distilled water is added dropwise to a solution of 1.85 g (4.4 mmol) of gallium(III) nitrate hydrate in 250 ml of distilled water. The product can be precipitated at pH 4 to 5 by addition of concentrated ammonia. The precipitate is separated off and washed with water. Drying gives a yellow crystalline solid which has a yellowish green fluorescence.

Yield: 1.2 g (1.35 mmol≙61.4% of theory).

Example 9

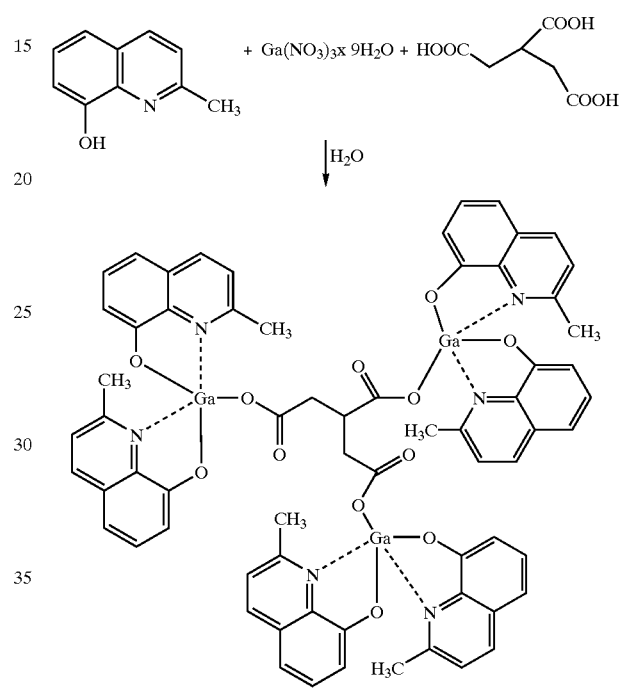

A solution of 1.0 g (6.3 mmol) of recrystallized 8-hydroxyquinaldine and 5.53 g (31.4 mmol) of tricarballyl acid in 400 ml of distilled water is added dropwise to a solution of 1.31 g (3.14 mmol) of gallium(III) nitrate hydrate in 100 ml of distilled water. The product can be precipitated at pH 4 to 5 by addition of concentrated ammonia. The precipitate is separated off and washed with water. Drying gives a light-yellow crystalline solid which has a yellow fluorescence.

Yield: 1.35 g (1 mmol≙95% of theory).

Examples, Physical Part

Example 1

The substance B1 according to the invention is used for constructing an organic light emitting diode OLED. The OLED is produced as follows:

1. Cleaning the ITO substrate

ITO-coated glass (Merck Balzers AG, FL, Part. No. 253 674 XO) is cut into 50 mm×50 mm pieces (substrates). The substrates are subsequently cleaned in a 3% strength aqueous Mukasol solution in an ultrasonic bath for 15 minutes. The substrates are then rinsed with distilled water and spun dry in a centrifuge. This rinsing and drying procedure is repeated 10 times.

2. Application of the ®Baytron P layer to the ITO

About 10 ml of the 1.3% strength polyethylenedioxythiophene/polysulphonic acid solution (Bayer AG, Baytron P) are filtered (Millipore HV, 0.45 μm). The substrate is subsequently placed on a spin coater and the filtered solution is distributed on the ITO-coated side of the substrate. The excess solution is subsequently spun off by rotation of the plate at 500 rpm for a period of 3 minutes. The substrate which has been coated in this way is then dried at 110° C. for 5 minutes on a hotplate. The thickness of the layer is 60 nm (Tencor, Alphastep 200).

3. Application of the hole conduction layer 5 ml of a 1.0% strength solution of phenylarnine (Agfa-Gevaert, compound Al) are filtered (Millipore HV, 0.45 μm) and distributed on the dried Baytron P layer. The excess solution is subsequently spun off by rotation of the plate at 500 rpm for 60 seconds. The substrate which has been coated in this way is then dried at 110° C. for 5 minutes on a hotplate. The total thickness of the layers is 130 mm.

4. Vapour deposition of the light-emitting/electron-injecting layer

A third organic layer, namely the substance B1 according to the invention, is applied by thermal vapour deposition to the two organic layers produced in this way. This is carried out in a vapour deposition unit (Leybold, Univex 350). The pressure in the vapour deposition unit during vapour deposition is $10^{-3}$ Pa and the deposition rate is 2 Å/sec. The total thickness of the 3 organic layers is 200 nm.

5. Vapour deposition of the metal cathode

A metal electrode is vapour-deposited onto the organic layer system. For this purpose, the substrate is placed with the organic layer system downwards on a perforated mask (hole diameter: 5 nm). At a pressure of $10^{-3}$ Pa, the elements Mg and Ag are vaporized simultaneously from two vapour deposition boats. The deposition rates are 28 Å/sec for Mg. The thickness of the vapour-deposited metal contacts is 500 nm.

The two electrodes of the organic LED are connected to a power source via electric leads. The positive pole is connected to the ITO electrode, the negative pole is connected to the MgAg electrode.

Above a voltage of only 4 volts, electroluminescence can be detected by means of a photodiode (EG&G C30809E). At a voltage of 8 volt, the current per unit area is 1 mA/cm² and the electroluminescence is readily visible. The colour of the electroluminescence has the colour values X=0.3915; Y=0.4982 (measured at 12 V). (Spectrometer: CDI-PDA, Sentronic GmbH).

Example 2

The substance B1 according to the invention is used for constructing an organic light emitting diode (OLED).

Production and electric actuation are carried out as described in Example 1, except that the substance B1 according to the invention is applied as third organic layer on the first two layers by coating from a 1% strength methanolic solution. The total thickness of the three organic layers is 150 nm.

Above a voltage of only 4 volt, electroluminescence can be detected by means of a photodiode (EG&G C30809E).

Although the present invention has been described in detail with reference to certain preferred versions thereof, other variations are possible. Therefore, the spirit and scope of the appended claims should not be limited to the description of the versions contained therein.

What is claimed is:

1. An electroluminescent assembly comprising:

a substrate;

an anode;

an electroluminescent element comprising (i) a hole injection zone and optionally one or more zones selected from the group consisting of (ii) a hole transport zone, (iii) an electroluminescent zone, (iv) an electron transport zone, and (v) an electron injection zone in the specified order, wherein each said zone (i), (ii), (iii), (iv) or (v) can assume a plurality of functions; and a cathode, wherein at least one of anode and the cathode is transparent in the visible spectral region, wherein the electroluminescent element contains a multinuclear metal complex and wherein the hole injection zone contains an uncharged or cationic polythiophene of the formula (I),

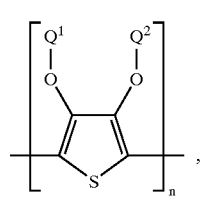

(I)

wherein $Q^1$ and $Q^2$ independently represent hydrogen, substituted or unsubstituted $(C_1-C_{20})$-alkyl, $CH_2OH$ or $(C_6-C_{14})$-aryl or $Q^1$ and $Q^2$ together represent $-(CH_2)_m-CH_2-$ wherein m represents 0 to 12, or $(C_6-C_{14})$-arylene, and n represents an integer from 2 to 10,000.

2. The electroluminescent assembly according to claim 1 further including at least one of an anion of a polymeric carboxylic acid and a polymeric sulphonic acid as a polyanion.

3. The electroluminescent assembly according to claim 1 further including at least one of polystyrenesulphonic acid and an alkali metal salt thereof as a counterion.

4. The electroluminescent assembly according to claim 1, wherein at least one of the hole injection and the hole transport zone contains an aromatic tertiary amino compound of the formula (II)

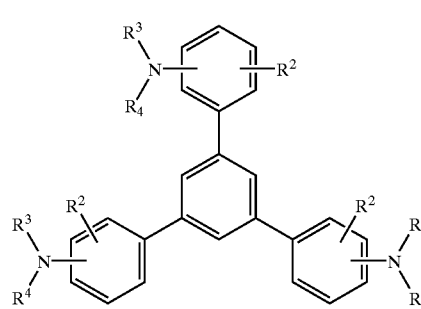

(II)

wherein

R² represents hydrogen, substituted or unsubstituted alkyl or halogen,

R³ and R⁴ independently represent substituted or unsubstituted $(C_1-C_{10})$-alkyl, alkoxycarbonyl-substituted $(C_1-C_{10})$-alkyl or substituted or unsubstituted aryl, aralkyl or cycloalkyl.

5. The electroluminescent assembly according to claim 4, wherein

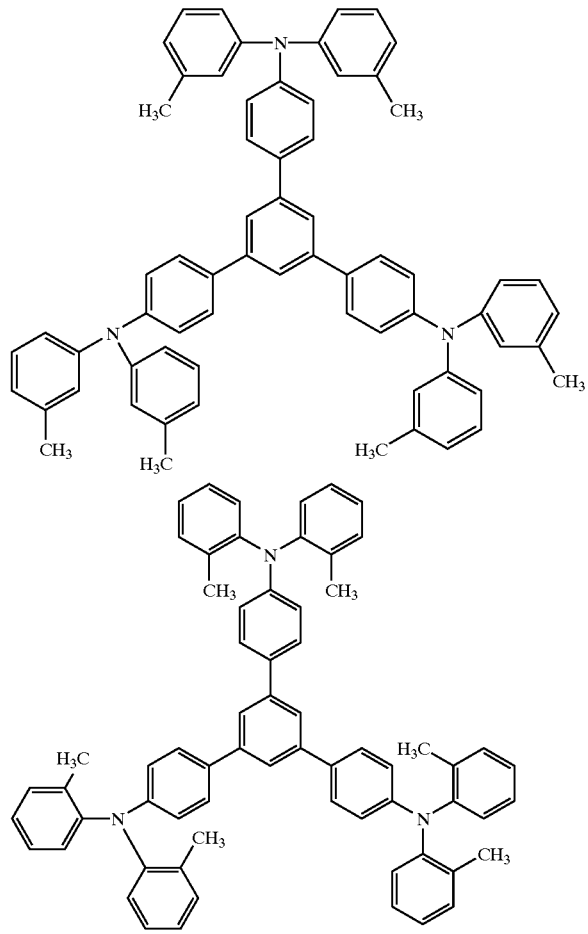

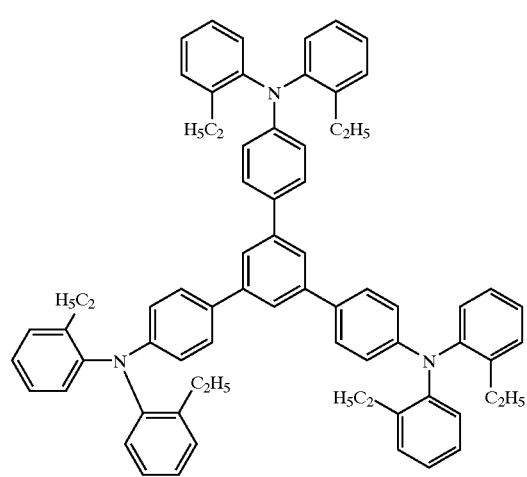

R² represents hydrogen or $(C_1-C_6)$-alkyl,

R³ and R⁴ independently represent $(C_1-C_6)$-alkyl, $(C_1-C_4)$-alkoxycarbonyl-$(C_1-C_6)$-alkyl or unsubstituted or $(C_1-C_4)$-alkyl- and/or $(C_1-C_4)$-alkoxy-substituted phenyl, naphthyl, phenyl-$(C_1-C_4)$-alkyl, naphthyl-$(C_1-C_4)$-alkyl, cyclopentyl or cyclohexyl.

6. The electroluminescent assembly according to claim 4 wherein the tertiary amino compound is selected from among the following compounds:

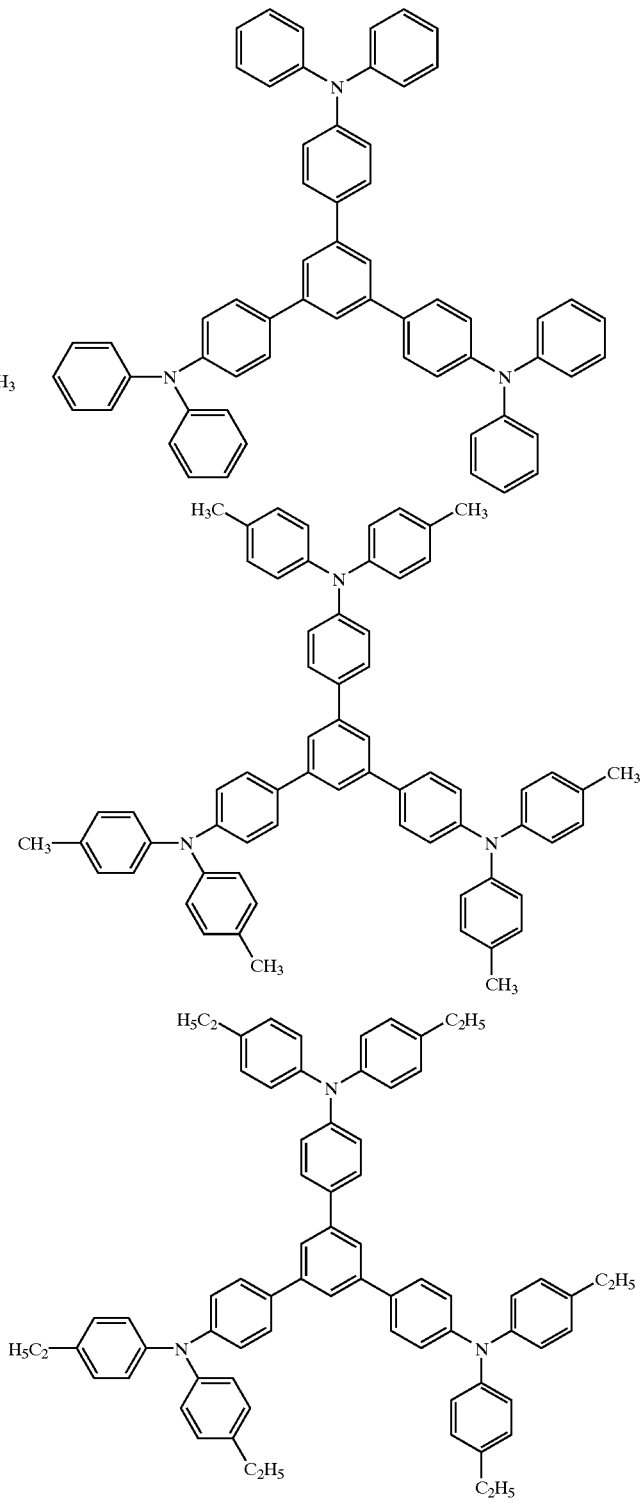

-continued
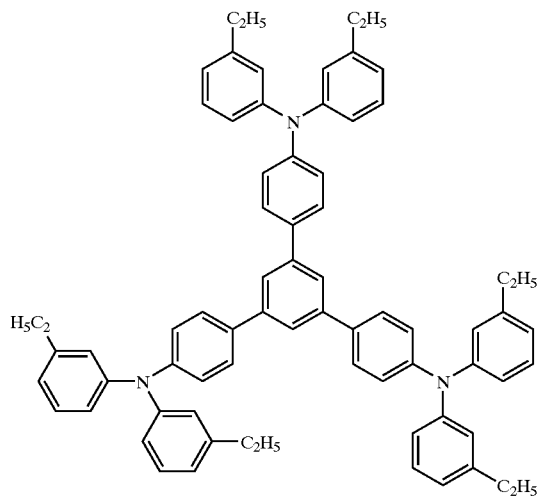
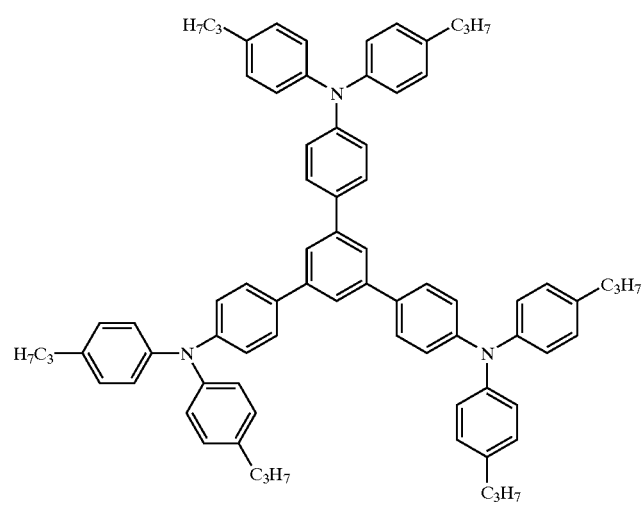
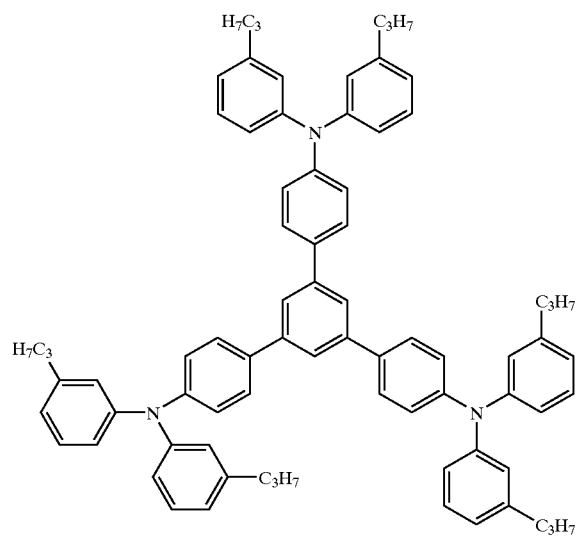
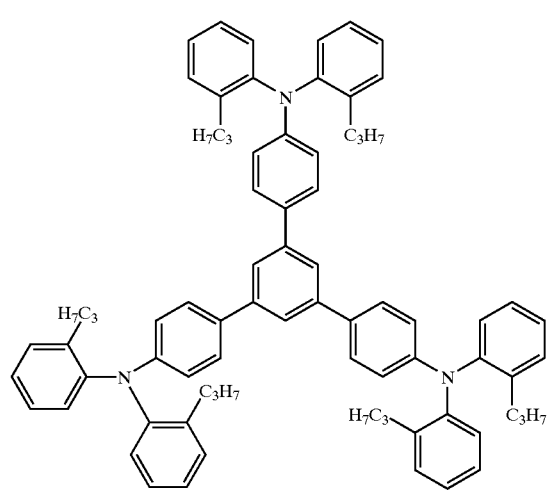
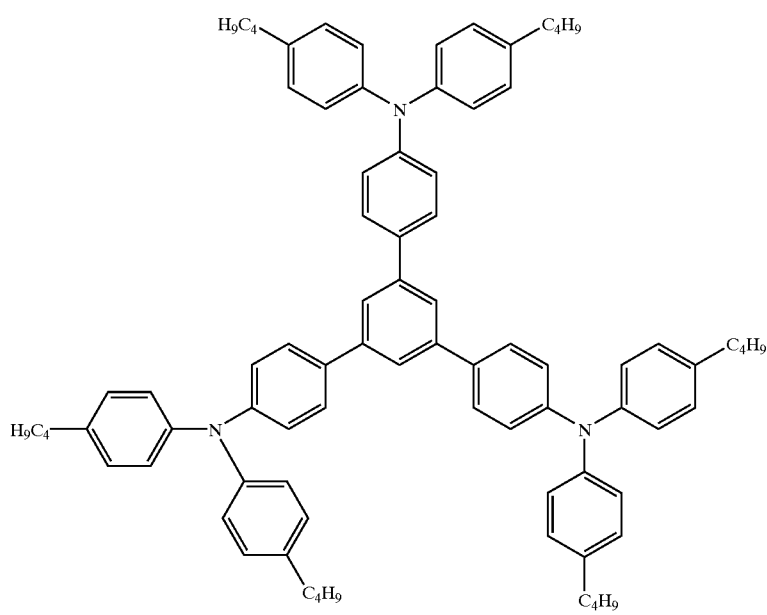

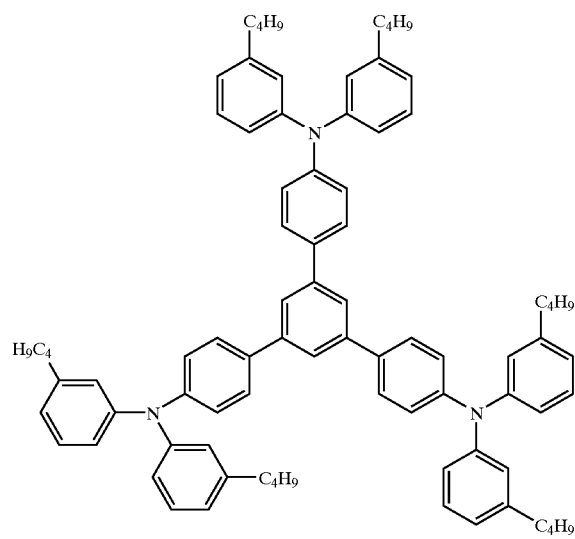
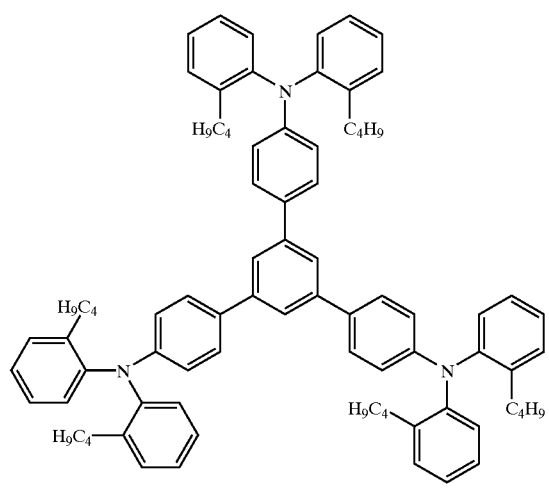
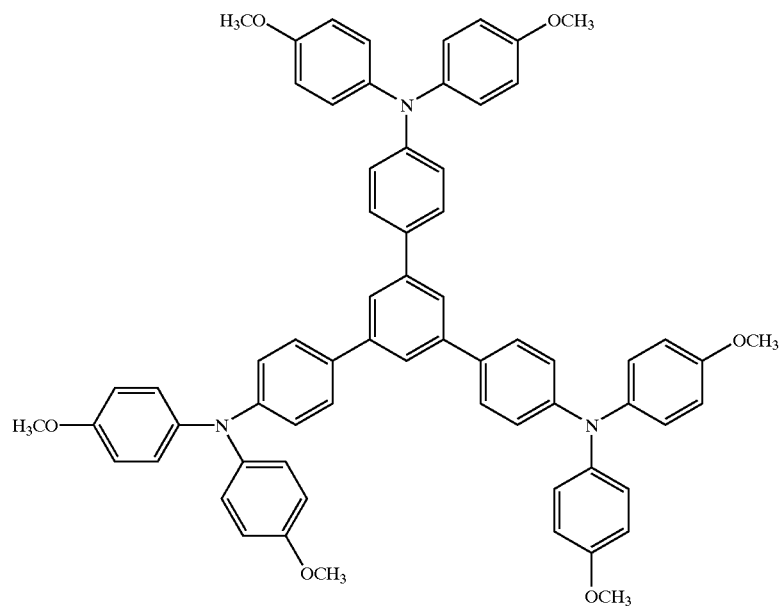
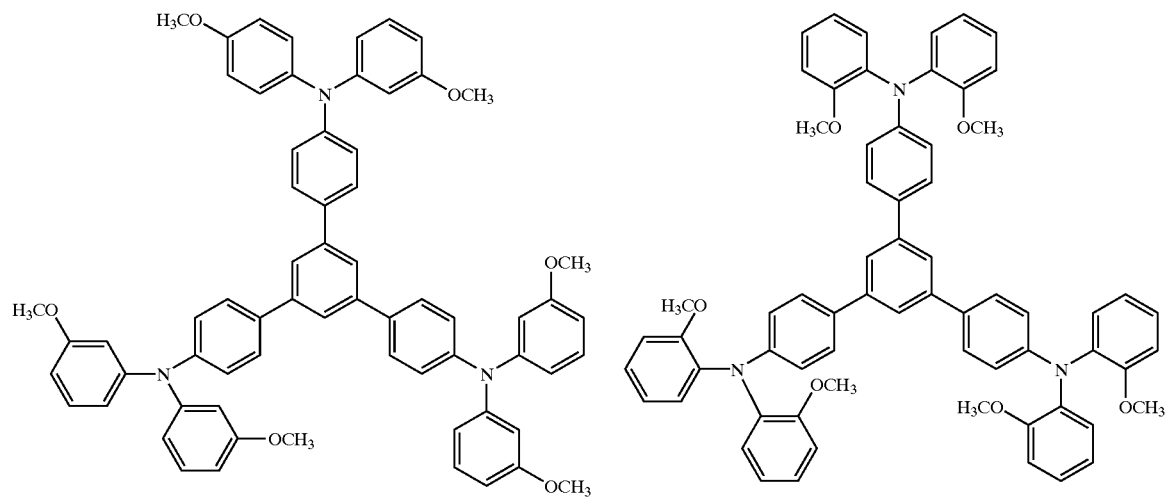

-continued
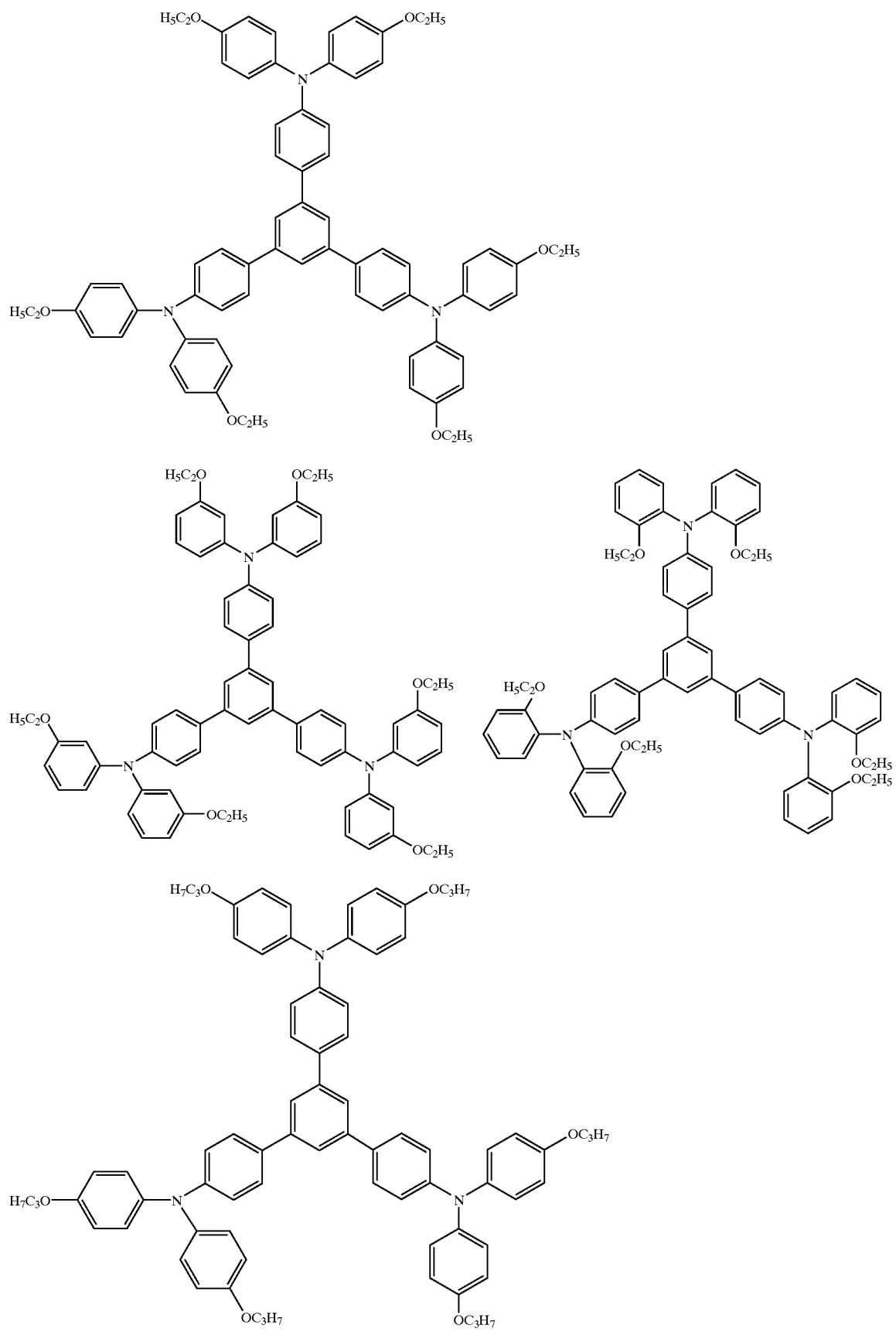

-continued
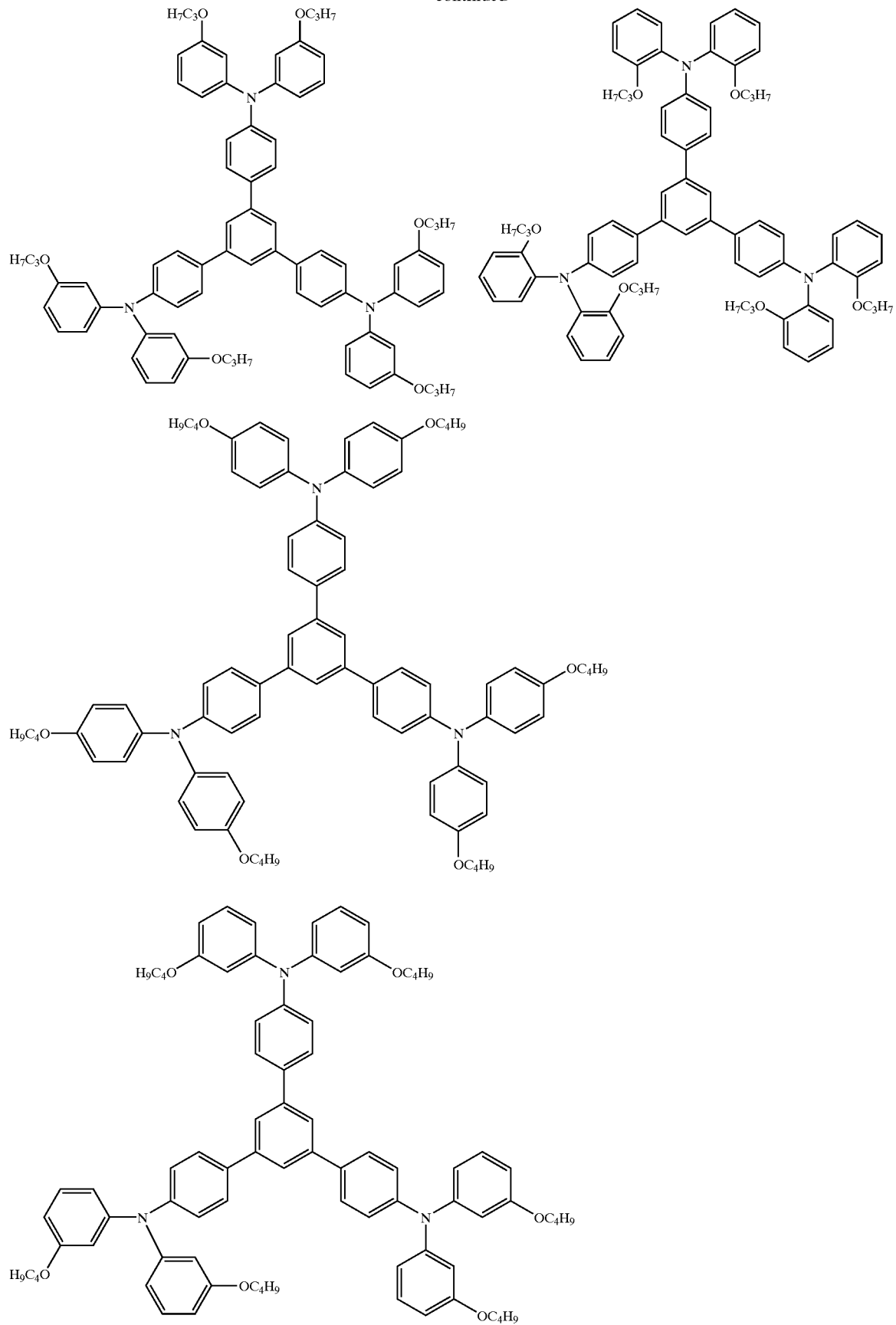

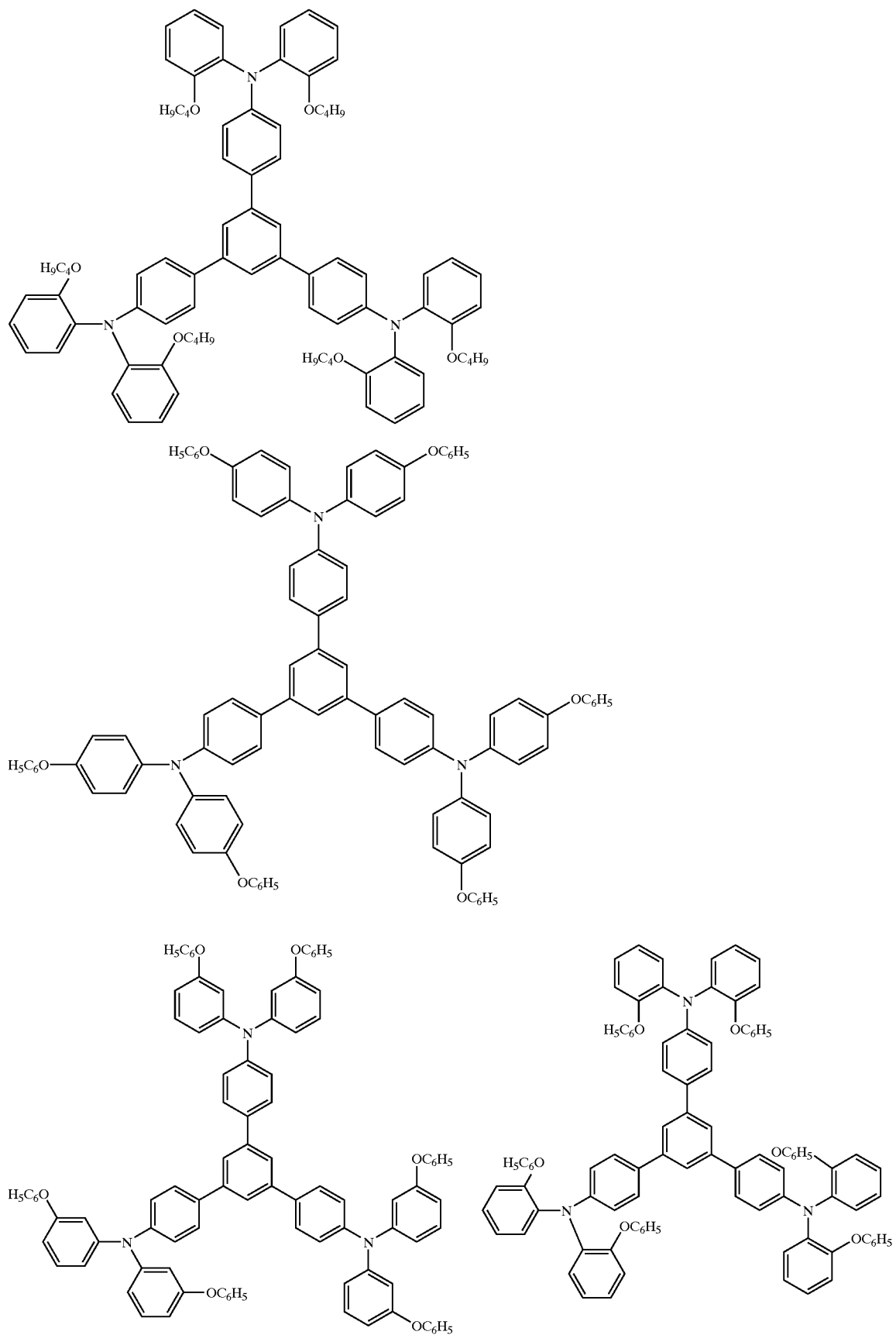

-continued
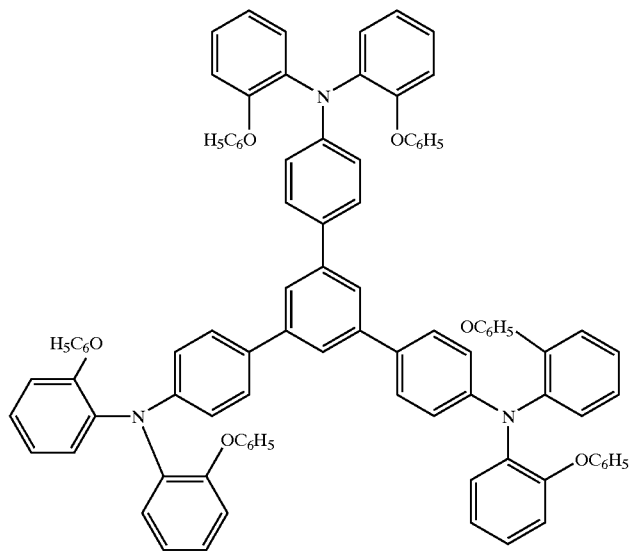
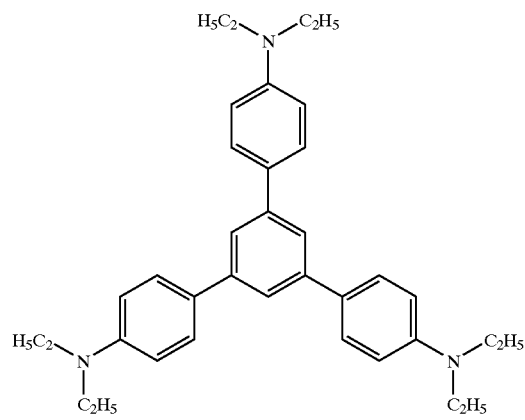
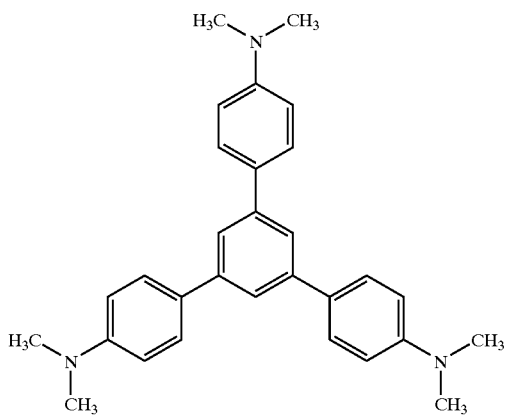
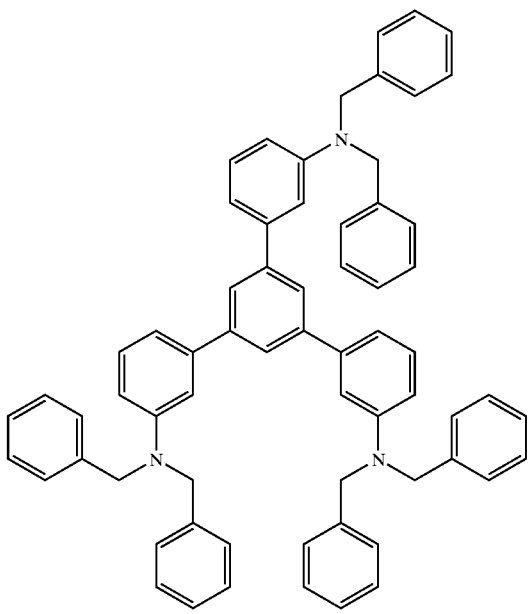
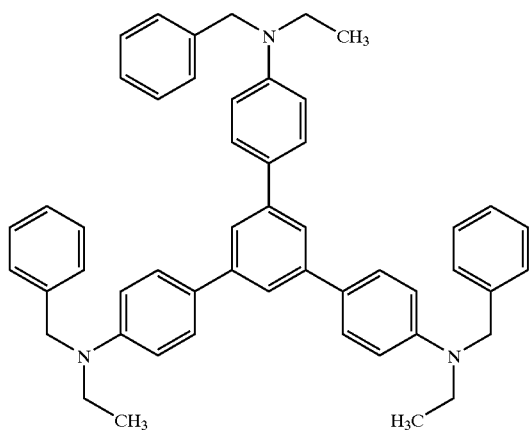

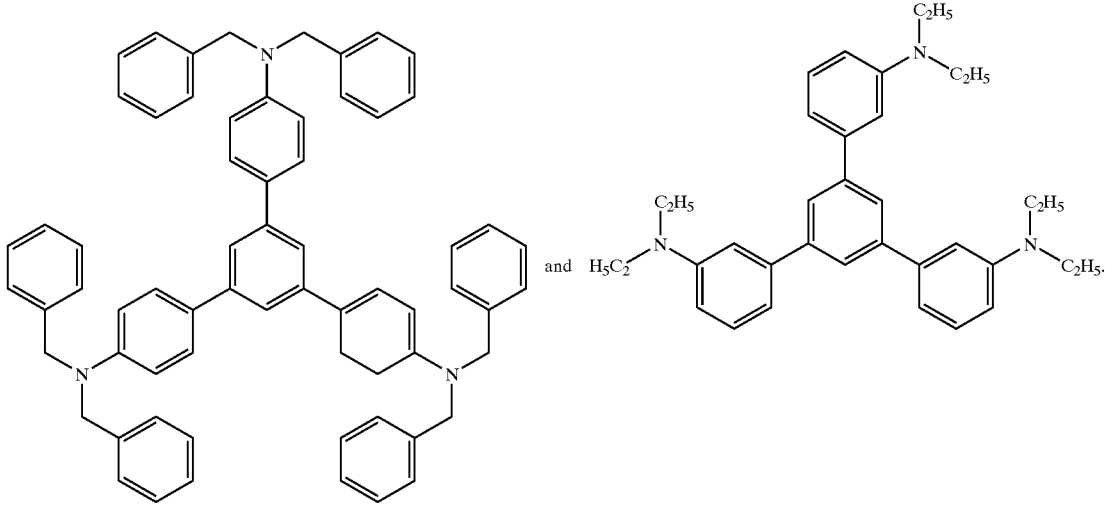

7. The electroluminescent assembly according to claim 1 further including a transparent binder selected from the group consisting of polycarbonates, polyester carbonates, copolymers of styrene, polysulphones, polymers based on vinyl-containing monomers, polyolefins, cyclic olefin copolymers and phenoxy resins.

8. An electroluminescent assembly comprising:
   a substrate;
   an anode;
   an electroluminescent element comprising (i) a hole injection zone and optionally one or more zones selected from the group consisting of (ii) a hole transport zone, (iii) an electroluminescent zone, (iv) an electron transport zone, and (v) an electron injection zone in the specified order, wherein each said zone (i), (ii), (iii), (iv) or (v) can assume a plurality of functions; and
   a cathode,
   wherein at least one of anode and the cathode is transparent in the visible spectral region, wherein the electroluminescent element contains a multinuclear metal complex and wherein the hole injection zone contains an uncharged or cationic polythiophene of the formula (Ia) or (Ib) or a mixture thereof,

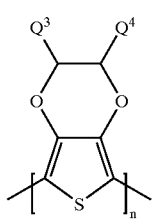

(Ia)

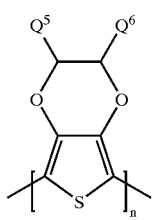

(Ib)

wherein
Q$^3$ and Q$^4$ independently represent hydrogen or substituted or unsubstituted (C$_1$–C$_{18}$)-alkyl, (C$_2$–C$_{12}$)-alkenyl, (C$_3$–C$_7$)-cycloalkyl, (C$_7$–C$_{15}$)-aralkyl, (C$_6$–C$_{10}$)-aryl, (C$_1$–C$_{18}$)-alkoxy or (C$_2$–C$_{18}$)-alkyloxy ester and Q$^5$ and Q$^6$ independently represent hydrogen or (C$_1$–C$_{18}$)-alkyl, (C$_2$–C$_{12}$)-alkenyl, (C$_3$–C$_7$)-cycloalkyl, (C$_7$–C$_{15}$)-aralkyl, (C$_6$–C$_{10}$)-aryl, (C$_1$–C$_{18}$)-alkoxy or (C$_2$–C$_{18}$)-alkyloxy ester which are each substituted by at least one sulphonate group, where, if Q$^5$ represents hydrogen, Q$^6$ is not hydrogen and vice versa, and n represents an integer from 2 to 10,000.

9. The electroluminescent assembly according to claim 8 wherein the cationic or uncharged polythiophene is selected from the group consisting of compounds having formulae (Ia-1) and (Ib-1),

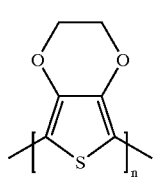

(Ia-1)

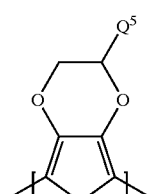

(Ib-1)

wherein Q$^5$ and n are as defined in claim 8.

10. An electroluminescent assembly comprising:
    a substrate,
    an anode,
    an electroluminescent element comprising one or more zones selected from the group consisting of (i) a hole injection zone, (ii) a hole transport zone, (iii) an electroluminescent zone, (iv) an electron transport zone, and (v) an electron injection zone in the specified order, wherein each said zone (i), (ii), (iii), (iv) or (v) can assume a plurality of functions, and a cathode, wherein at least one of the anode and the cathode is transparent in the visible spectral region, and wherein the electroluminescent element contains a multinuclear metal complex which is selected from the group of compounds having formulae (III)a, (III)b and (III)c:

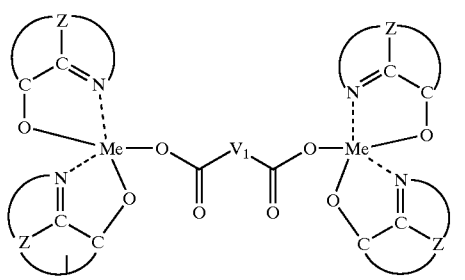

(III)a and

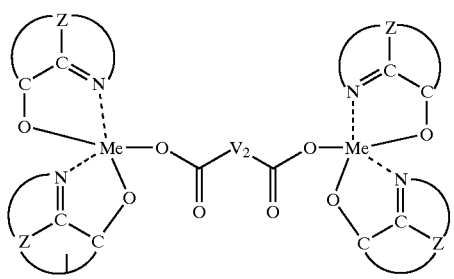

(III)b and

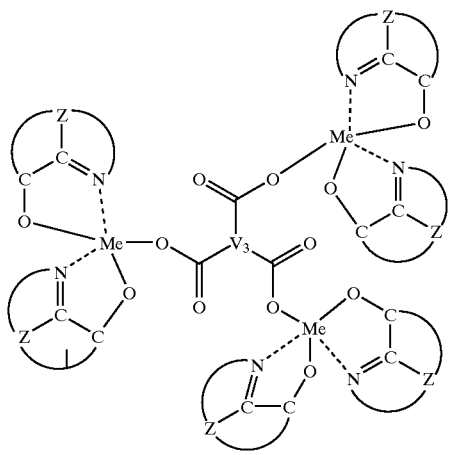

(III)c wherein

Me represents a metal, $V_1$ represents a substituted or unsubstituted and/or branched or unbranched alkylene radical, cycloalkylene radical or poly(oxyalkylene) radical, $V_2$ represents a substituted or unsubstituted and/or branched or unbranched alkenylene radical or alkynylene radical, $V_3$ represents a substituted or unsubstituted and/or branched or unbranched alkylene radical, and Z represents atoms which complete a moiety which comprises at least 2 fused rings.

11. The electroluminescent assembly according to claim 10, wherein Me represents a trivalent metal which forms chelates.

12. The electroluminescent assembly according to claim 10, wherein the hole injection zone contains an uncharged or cationic polythiophene of the formula (I),

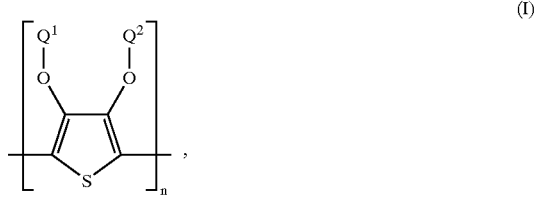

(I)

wherein $Q^1$ and $Q^2$ independently represent hydrogen, substituted or unsubstituted $(C_1$–$C_{20})$-alkyl, $CH_2OH$ or $(C_6$–$C_{14})$-aryl or $Q^1$ and $Q^2$ together represent —$(CH_2)_m$—$CH_2$— wherein m represents 0 to 12, or $(C_6$–$C_{14})$-arylene, and n represents an integer from 2 to 10,000.

13. The electroluminescent assembly according to claim 12 further including at least one of an anion of a polymeric carboxylic acid and a polymeric sulphonic acid as a polyanion.

14. The electroluminescent assembly according to claim 10, wherein the hole injection zone contains an uncharged or cationic polythiophene of the formula (Ia) or (Ib) or a mixture thereof,

(Ia)

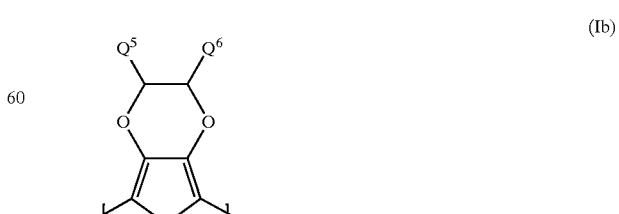

(Ib)

wherein

Q³ and Q⁴ independently represent hydrogen or substituted or unsubstituted $(C_1–C_{18})$-alkyl, $(C_2–C_{12})$-alkenyl, $(C_3–C_7)$-cycloalkyl, $(C_7–C_{15})$-aralkyl, $(C_6–C_{10})$-aryl, $(C_1–C_{18})$-alkoxy or $(C_2–C_{18})$-alkyloxy ester and Q⁵ and Q⁶ independently represent hydrogen or $(C_1–C_{18})$-alkyl, $(C_2–C_{12})$-alkenyl, $(C_3–C_7)$-cycloalkyl, $(C_7–C_{15})$-aralkyl, $(C_6–C_{10})$-aryl, $(C_1–C_{18})$-alkoxy or $(C_2–C_{18})$-alkyloxy ester which are each substituted by at least one sulphonate group, where, if Q⁵ represents hydrogen, Q⁶ is not hydrogen and vice versa, and n represents an integer from 2 to 10,000.

15. The electroluminescent assembly according to claim 10, wherein at least one of the hole injection and the hole transport zone contains an aromatic tertiary amino compound of the formula (II)

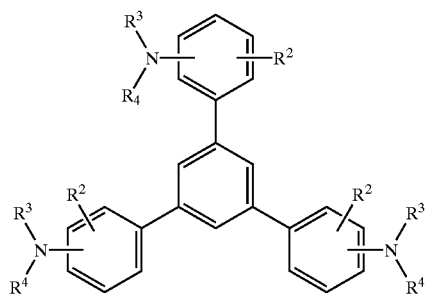

(II)

wherein

R² represents hydrogen, substituted or unsubstituted alkyl or halogen,

R³ and R⁴ independently represent substituted or unsubstituted $(C_1–C_{10})$-alkyl, alkoxycarbonyl-substituted $(C_1–C_{10})$-alkyl or substituted or unsubstituted aryl, aralkyl or cycloalkyl.

16. The electroluminescent assembly according to claim 10 further including a transparent binder selected from the group consisting of polycarbonates, polyester carbonates, copolymers of styrene, polysulphones, polymers based on vinyl-containing monomers, polyolefins, cyclic olefin copolymers and phenoxy resins.

17. An electroluminescent assembly comprising:

a substrate, an anode, an electroluminescent element comprising one or more zones selected from the group consisting of (i) a hole injection zone, (ii) a hole transport zone, (iii) an electroluminescent zone, (iv) an electron transport zone, and (v) an electron injection zone in the specified order, wherein each said zone (i), (ii), (iii), (iv) or (v) can assume a plurality of functions, and a cathode, wherein at least one of the anode and the cathode is transparent in the visible spectral region, and wherein the electroluminescent element contains a multinuclear metal complex selected from the group consisting of compounds having formulae B1, B2, B3, B4, B5, B6, B7, B8, B9, B10, and B11:

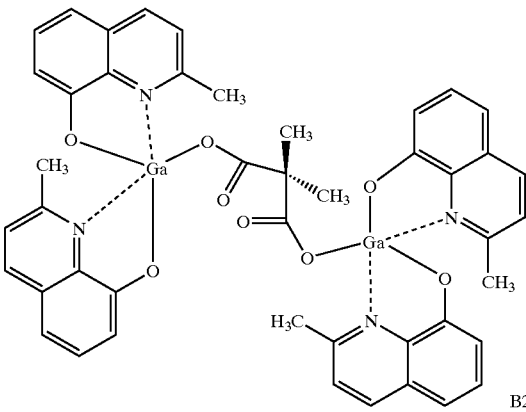

B1

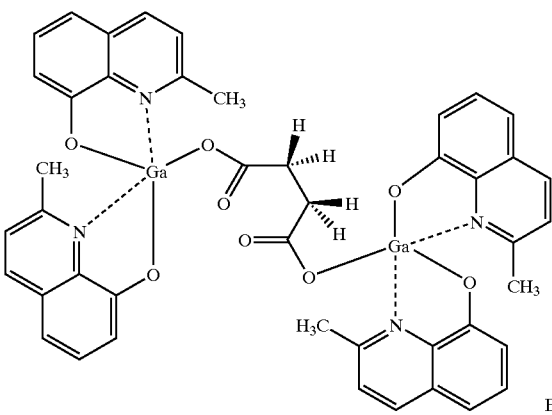

B2

B3

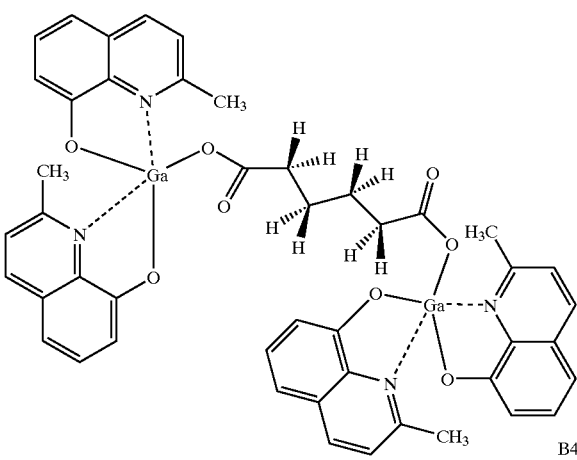

B4

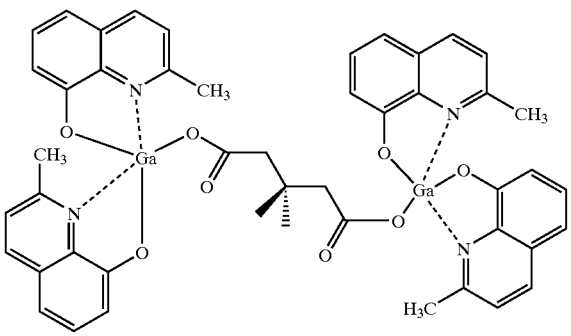

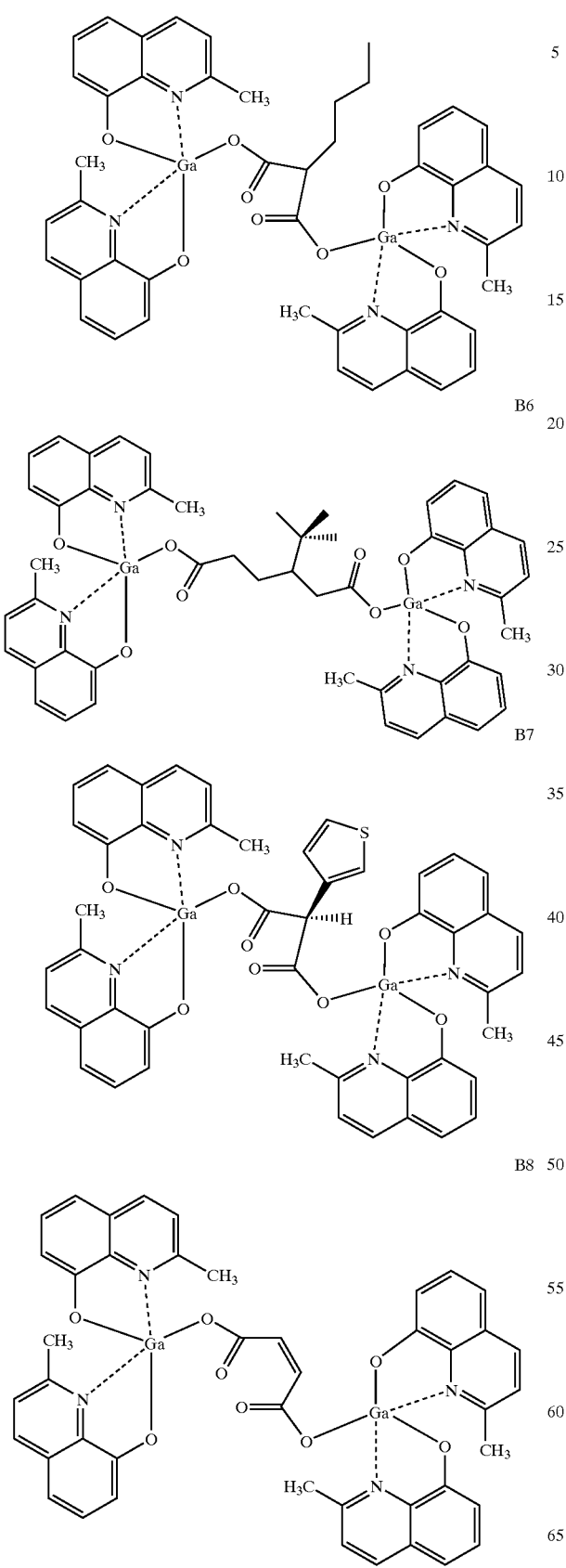
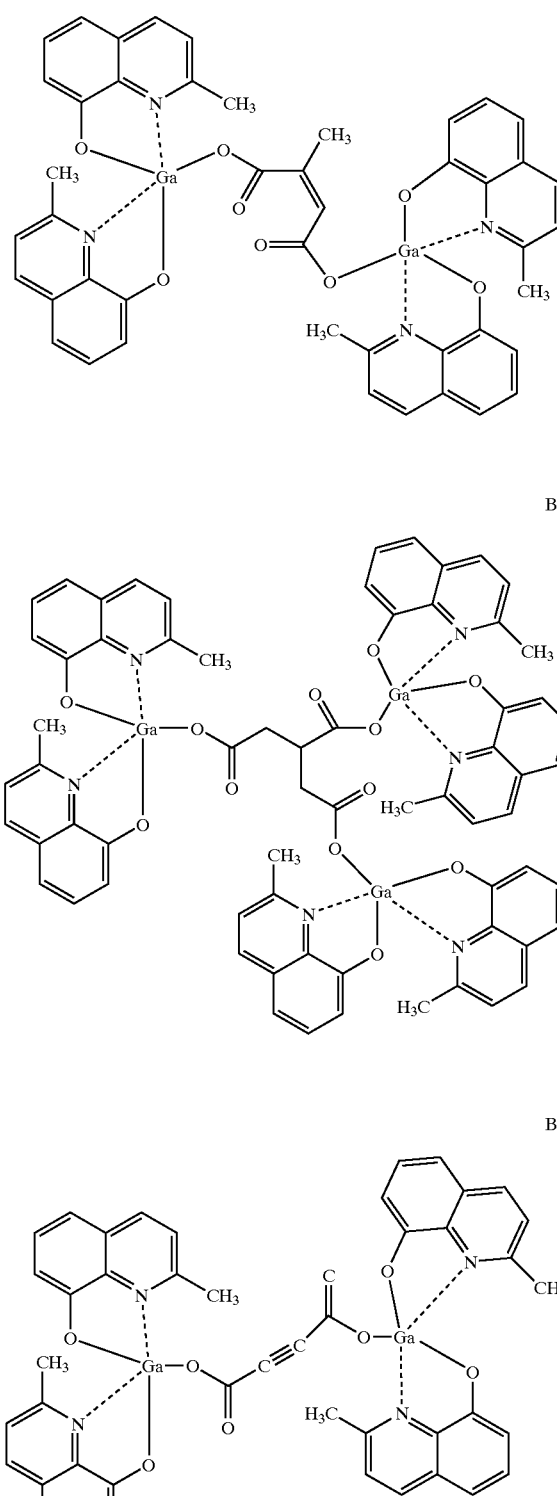
18. The electroluminescent assembly according to claim 17, wherein the hole injection zone contains an uncharged or cationic polythiophene of the formula (I),

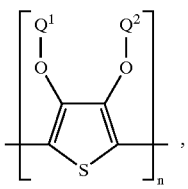
(I)

wherein
Q¹ and Q² independently represent hydrogen, substituted or unsubstituted $(C_1-C_{20})$-alkyl, $CH_2OH$ or $(C_6-C_{14})$-aryl
or
Q¹ and Q² together represent $-(CH_2)_m-CH_2-$
wherein m represents 0 to 12, or $(C_6-C_{14})$-arylene, and
n represents an integer from 2 to 10,000.

19. The electroluminescent assembly according to claim 18 further including at least one of an anion of a polymeric carboxylic acid and a polymeric sulphonic acid as a polyanion.

20. The electroluminescent assembly according to claim 17, wherein the hole injection zone contains an uncharged or cationic polythiophene of the formula (Ia) or (Ib) or a mixture thereof,

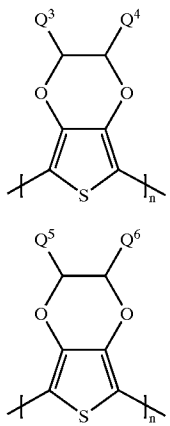

(Ia)

(Ib)

wherein
Q³ and Q⁴ independently represent hydrogen or substituted or unsubstituted $(C_1-C_{18})$-alkyl, $(C_2-C_{12})$-alkenyl, $(C_3-C_7)$-cycloalkyl, $(C_7-C_{15})$-aralkyl, $(C_6-C_{10})$-aryl, $(C_1-C_{18})$-alkoxy or $(C_2-C_{18})$-alkyloxy ester and Q⁵ and Q⁶ independently represent hydrogen or $(C_1-C_{18})$-alkyl, $(C_2-C_{12})$-alkenyl, $(C_3-C_7)$-cycloalkyl, $(C_7-C_{15})$-aralkyl, $(C_6-C_{10})$-aryl, $(C_1-C_{18})$-alkoxy or $(C_2-C_{18})$-alkyloxy ester which are each substituted by at least one sulphonate group, where, if Q⁵ represents hydrogen, Q⁶ is not hydrogen and vice versa, and n represents an integer from 2 to 10,000.

21. The electroluminescent assembly according to claim 17, wherein at least one of the hole injection and the hole transport zone contains an aromatic tertiary amino compound of the formula (II)

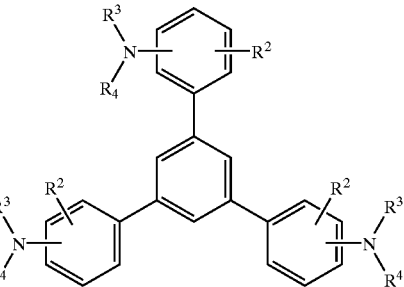

(II)

wherein
R² represents hydrogen, substituted or unsubstituted alkyl or halogen,
R³ and R⁴ independently represent substituted or unsubstituted $(C_1-C_{10})$-alkyl, alkoxycarbonyl-substituted $(C_1-C_{10})$-alkyl or substituted or unsubstituted aryl, aralkyl or cycloalkyl.

22. The electroluminescent assembly according to claim 17 further including a transparent binder selected from the group consisting of polycarbonates, polyester carbonates, copolymers of styrene, polysulphones, polymers based on vinyl-containing monomers, polyolefins, cyclic olefin copolymers and phenoxy resins.

* * * * *